United States Patent
Busch et al.

(10) Patent No.: US 7,546,837 B2
(45) Date of Patent: *Jun. 16, 2009

(54) INTERFACE WITH ROLLING DIAPHRAGM

(75) Inventors: Lance Busch, Trafford, PA (US); Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/374,580

(22) Filed: Mar. 13, 2006

(65) Prior Publication Data

US 2006/0207599 A1    Sep. 21, 2006

Related U.S. Application Data

(60) Provisional application No. 60/662,314, filed on Mar. 16, 2005.

(51) Int. Cl.
*A62B 18/08* (2006.01)
*A62B 18/02* (2006.01)

(52) U.S. Cl. .............................. 128/206.24; 128/206.21

(58) Field of Classification Search ................. 128/846, 128/859–862, 206.12, 206.18, 206.21, 206.24, 128/206.26–29, 205.21, 857, 863, 200.24, 128/201.24, 202.27, 203.29
See application file for complete search history.

(56) References Cited

U.S. PATENT DOCUMENTS

| 2,130,555 | A | * | 9/1938 | Malcom | ....................... 55/377 |
| 2,428,451 | A | * | 10/1947 | Emerson | ................. 128/205.13 |
| 4,069,516 | A | | 1/1978 | Watkins, Jr. | |
| 4,498,472 | A | * | 2/1985 | Tanaka | ................... 128/205.17 |
| 4,907,584 | A | | 3/1990 | McGinnis | |
| 5,074,297 | A | * | 12/1991 | Venegas | ................. 128/205.25 |
| 5,349,949 | A | | 9/1994 | Schegerin | |
| 5,540,223 | A | | 7/1996 | Starr et al. | |
| 5,647,357 | A | | 7/1997 | Barnett et al. | |
| 6,155,253 | A | | 12/2000 | Gamberini | |
| 6,474,339 | B1 | * | 11/2002 | Grosbois et al. | ............ 128/848 |
| 6,651,663 | B2 | | 11/2003 | Barnett et al. | |
| 6,729,333 | B2 | * | 5/2004 | Barnett et al. | .......... 128/207.13 |

(Continued)

FOREIGN PATENT DOCUMENTS

WO    WO 01/97893 A1    12/2001

(Continued)

OTHER PUBLICATIONS

Tiara Medical Systems, Inc., "Advantage HUSH Nasal Mask", product brochure.

*Primary Examiner*—Justine R Yu
*Assistant Examiner*—Annette F Dixon
(74) *Attorney, Agent, or Firm*—Michael W. Haas

(57) ABSTRACT

A patient interface gas delivery mask having a rolling diaphragm that connects a seal member forming a cushion which contacts the patient's face with a mask shell or that connects a conduit coupling member with the mask shell. The rolling diaphragm of the present invention allows the cushion to self align to the patient's face and allows relative movement between the seal member and the mask shell. This prevents torque acting of a conduit coupled to the mask shell from being translated to the seal member, which might otherwise dislodge the seal member creating unwanted gas leakage at the seal member-patient interface.

15 Claims, 22 Drawing Sheets

U.S. PATENT DOCUMENTS

| | | | |
|---|---|---|---|
| 6,772,760 B2 | 8/2004 | Frater et al. | |
| 2002/0174868 A1* | 11/2002 | Kwok et al. | 128/205.25 |
| 2003/0019495 A1 | 1/2003 | Palkon et al. | |
| 2003/0089372 A1* | 5/2003 | Frater et al. | 128/206.24 |
| 2004/0025883 A1 | 2/2004 | Eaton et al. | |
| 2004/0045551 A1 | 3/2004 | Eaton et al. | |
| 2004/0112385 A1 | 6/2004 | Drew et al. | |
| 2004/0144386 A1* | 7/2004 | Frater et al. | 128/206.24 |
| 2004/0182398 A1* | 9/2004 | Sprinkle et al. | 128/207.13 |
| 2005/0039753 A1* | 2/2005 | Schumacher | 128/206.27 |
| 2005/0072428 A1* | 4/2005 | Ho et al. | 128/205.25 |
| 2005/0076913 A1 | 4/2005 | Ho et al. | |
| 2005/0150495 A1* | 7/2005 | Rittner et al. | 128/205.13 |
| 2006/0130844 A1* | 6/2006 | Ho et al. | 128/206.24 |
| 2006/0196509 A1* | 9/2006 | Drew et al. | 128/206.21 |
| 2006/0213520 A1* | 9/2006 | Frater et al. | 128/206.24 |

FOREIGN PATENT DOCUMENTS

| | | | |
|---|---|---|---|
| WO | WO 2004/022146 A1 | 3/2004 | |

* cited by examiner

INTERFACE WITH ROLLING DIAPHRAGM

CROSS-REFERENCE TO RELATED APPLICATIONS

This application claims priority under 35 U.S.C. § 119(e) from provisional U.S. patent application No. 60/662,314 filed Mar. 16, 2005 the contents of which are incorporated herein by reference.

BACKGROUND OF THE INVENTION

1. Field of the Invention

The present invention generally relates to a patient interface for use in a pressure support system that supplies a flow of gas to the airway of a patient, and, in particular, to a patient interface that includes a flexible connecting member that couples a seal member and mask shell to allow angular movement therebetween.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), Cheyne-Stokes respiration, or congestive heart failure.

Non-invasive ventilation and pressure support therapies involve the placement of a patient interface, which is typically a nasal or nasal/oral mask, on the face of a patient. The patient interface couples the ventilator or pressure support system with the airway of the patient, so that a flow of breathing gas can be delivered from the flow/pressure generating device to the airway of the patient.

Because such patient interfaces are typically worn for an extended period of time, a variety of concerns must be taken into consideration. For example, in providing CPAP to treat OSA, the patient normally wears the patient interface all night long while he or she sleeps. One concern in such a situation is that the patient interface is as comfortable as possible, otherwise the patient may avoid wearing the interface device, defeating the purpose of the prescribed pressure support therapy. It is also important that the patient interface provide a tight enough seal against the user's face without discomfort. A problem arises in that in order for the mask to maintain a seal without any undue gas leaks around the periphery of the mask, the mask may be compressed against the patient's face with too much force, causing discomfort.

Typically, patient interfaces include a mask shell having a cushion (also referred to as a seal or seal member) attached to the shell. The cushion contacts the surface of the user. The mask shell and cushion are held in place by a headgear that wraps around the head of the user. The patient interface and headgear form a patient interface assembly. A typical headgear includes flexible, adjustable straps that extend from the mask to attach the mask to the patient.

A variety of techniques have been attempted to strike a balance between patient comfort and leak minimization. For example, it is known to form the cushion from a soft material, provide multiple flaps in the cushion, contour the cushion to match the human face, and form the cushion from a material that can be customized to the features of the user. It is also known to provide adjustability for the patient interface on the user, for example, by providing an adjustable forehead assembly. However, these patient interfaces may not meet all the needs of the patient population.

SUMMARY OF THE INVENTION

Accordingly, it is an object of the present invention to provide a patient interface that addresses the above-identified concerns and that overcomes the shortcomings of conventional patient interfaces. This object is achieved according to one embodiment of the present invention by providing a patient interface that includes a mask shell having a first side defined generally in a first plane and a second side opposite the first side. The patient interface also includes a seal member having a first end portion adapted to contact a user's face and a second end portion opposite the first end portion. The second end portion is disposed generally in the first plane. A flexible connecting member is positioned between the first side of the mask shell and the second end portion of the seal member. The flexible connecting member extends between the mask shell and the seal member generally in the first plane such that the flexible connecting member allows angular movement between the seal member and the mask shell.

In a further embodiment, this object is achieved by providing a patient interface that includes a mask shell and a seal member. The mask shell includes a first side, a second side opposite the first side, and first opening defined in the first side. The seal member has a first end portion adapted to contact a user's face, a second end portion opposite the first end portion, and a second opening defined in the second end portion. The first opening of the mask shell is larger than the second opening in the seal member. A flexible connecting member is positioned between the mask shell and the second end portion coupling the second end portion of the seal member with the first side of the mask shell.

In a still further embodiment, this object is achieved by providing a patient interface that includes a mask shell having a first side and a second side opposite the first side. The patient interface also includes a seal member having a first end portion adapted to contact a user's face and a second end portion opposite the first end portion. An annular flexible connecting member is positioned between the mask shell and the second end portion of the seal member. The flexible coupling connects the second end portion of the seal member with the first side of the mask shell. A dimension of the connecting member at a first location around a perimeter of the connecting member is different from a corresponding dimension at a second location of the connecting member to provide a different degree of flexibility for the connecting member between the first location and the second location.

In yet another embodiment, this object is achieved by providing a patient interface that includes a conduit coupling member having a first end portion and a second end portion, a mask shell having a first side and a second side opposite the first side, a seal member, and a flexible connecting member. The seal member has a first end portion adapted to contact a user's face and a second end portion opposite the first end portion that is coupled to the second side of the mask shell. The flexible connecting member is positioned between the first side of the mask shell and the second end portion of the conduit coupling member. The flexible connecting member extends between the mask shell and the conduit coupling member such that the flexible connecting member allows angular movement between the mask shell and the conduit coupling member.

In yet another embodiment of the present invention, this object is achieved by providing a patient interface that includes a mask shell having a first side and a second side generally opposite the first side, a seal member, and a flexible connecting member. The seal member has a first end portion adapted to contact a user's face and a second end portion opposite the first end portion adapted to be coupled to the mask shell. The first end portion has a first area and the second end portion has a second area. The flexible connecting member is positioned between the second side of the mask shell and the second end portion of the seal member to allow angular movement between the seal member and the mask shell. In addition, the first area is greater than the second area.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", an and "the" include plural referents unless the context clearly dictates otherwise.

DETAILED DESCRIPTION OF THE EXEMPLARY EMBODIMENTS

In describing the presently preferred embodiments of the invention, the terms "horizontal" and "vertical" refer to the orientation of the patient interfaces as illustrated in the accompanying drawings. More specifically, "horizontal" refers to a left-right or side-to-side direction, and "vertical" refers to an up-down or top-bottom direction.

FIGS. 1-5 illustrate a first exemplary embodiment of a patient interface 10 according to the principles of the present invention. Patient interface 10 communicates a flow of breathing gas between the patient's airway and a flow/pressure generating device 12, such as a ventilator, pressure support system, such as a CPAP, or a variable pressure device, e.g., a BiPAP® device or C-Flex device, both of which are manufactured and distributed by Respironics, Inc. of Pittsburgh, Pa., or an auto-titration pressure support system. A BiPAP® device is a bi-level device in which the pressure provided to the patient varies with the patient's respiratory cycle, so that a higher pressure is delivered during inspiration than during expiration. A C-Flex device is a device in which the pressure delivered to the patient is lowered during expiration in proportion to the patient flow. An auto-titration pressure support system is a system in which the pressure varies with the condition of the patient, such as whether the patient is snoring or experiencing an apnea or hypopnea. For present purposes, flow/pressure generating device 12 is any device that provides a flow of gas to an airway of a patient, including positive and negative pressure generating devices.

Figure 18:
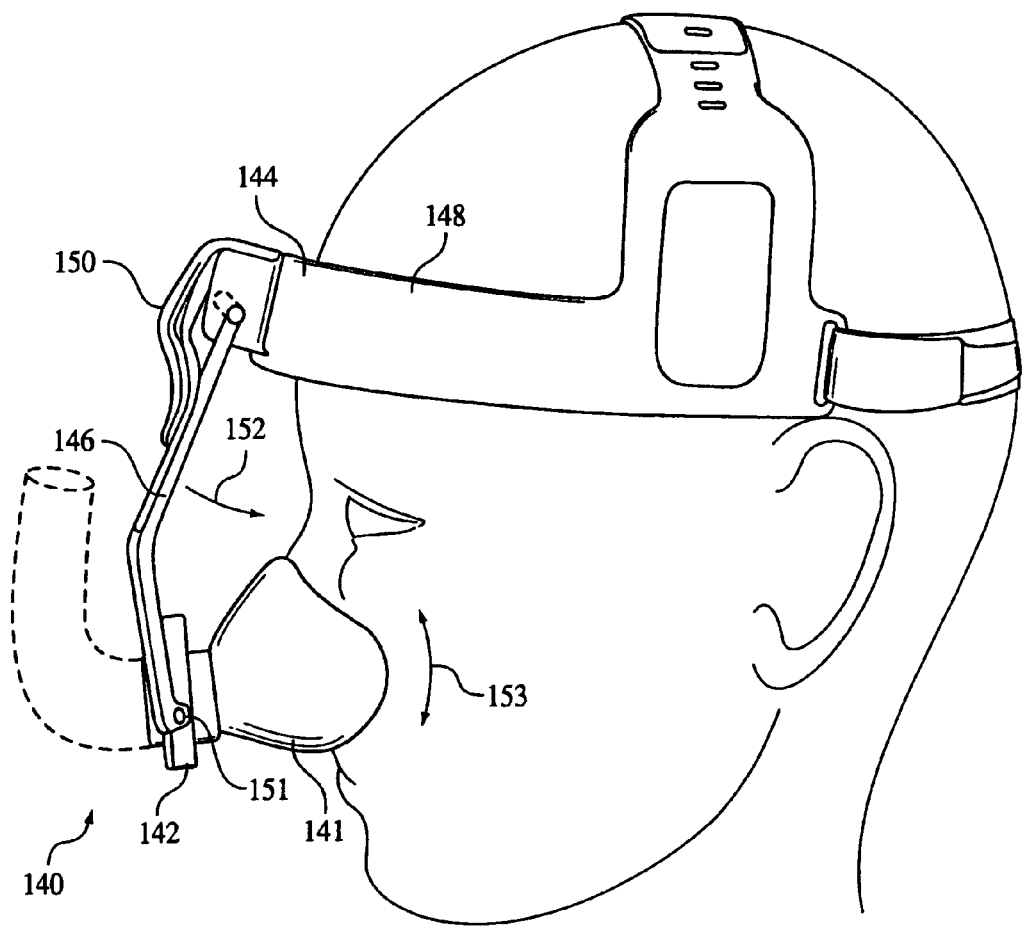
FIG. 18 is a side view of a patient interface according to a sixth embodiment of the patient interface according to the principles of the of the present invention also shown worn on a patient.

The system for delivering a breathing gas to a patient according to the present invention comprises a flow/pressure generating device 12 that produces a flow of gas, a conduit 14, which is also referred to as a patient circuit, having a first end portion 16 operatively coupled to the gas flow generating device and a second end portion 18. During operation of the system, conduit 14 carries the flow of gas from flow/pressure generating device 12 to patient interface 10, which is coupled to second end portion 18 of conduit 14. A headgear assembly (not shown in FIGS. 1-5) attaches the patient interface to the patient's head. An exemplary embodiment of a headgear assembly is shown in FIG. 18. It is to be understood that the present invention contemplates using any conventional headgear for attaching patient interface 10 to the patient.

Communicating a flow of breathing gas between the patient's airway and a flow/pressure generating device 12 includes exhausting a flow of gas from the system to ambient atmosphere. Exhausting gas from the system is accomplished via an exhaust assembly, generally indicated at 19, provided in conduit 14 in the patient interface. Exhaust assembly 19 is typically a fixed opening formed in the conduit that provides a path from the interior of the conduit to the ambient atmosphere. It is to be understood that the present invention contemplates using any conventional exhaust assembly with the patient interfaces of the present invention, including providing the exhaust assembly on the mask shell, the seal member, the conduit coupling member, the conduit, at a joint between any of these elements, or any combination thereof. It is to be further understood that other accessories used in a pressure support system, such as a humidifier, pressure sensor, flow sensor, temperature sensor, humidity sensor, bacteria filter, etc. can be used in conjunction with the patient interface of the present invention.

In the embodiment illustrated in FIGS. 1-5, patient interface 10 is a nasal mask assembly that communicates a flow of gas with the nares of the user. However, the present invention contemplates that other devices for communicating a flow of gas to an airway of a patient, such as an oral mask that covers the mouth, a nasal cannula, a mouthpiece, or combination nasal/oral mask, are suitable for use as patient interface 10.

Patient interface 10 includes a seal member 20, which contacts the patient's face, a mask shell 22, and a conduit coupling member 24. Seal member 20 shown in FIGS. 1-5 corresponds to the seal used with the patient interface described in U.S. Pat. Nos. 6,651,663 and 6,729,333, the contents of which are incorporated herein by reference. Seal member 20 is preferably defined from a unitary piece of soft, cushiony, elastomeric material, such as silicone, appropriately soft thermoplastic elastomers, closed cell foam, gel material, or any other material suitable for use as a patient-contacting seal. Seal member 20 has a first end portion 26 and a second end portion 28 generally opposite the first end portion with a nose receiving cavity 30 defined in the seal member. First end portion 26 is adapted to contact the patient's face and includes a first opening 32 to allow passage of a least a portion of the patient's nose into nose receiving cavity 30. Seal member 20 includes a neck portion 34 and a second opening 36 defined in neck portion 34. In the illustrated embodiment, neck portion 34 is relatively thick as compared to a remainder of the seal member 20.

Patient interface 10 further includes a flexible connecting member 38, which is referred to interchangeably as a rolling diaphragm, that is operatively connected between seal member 20 and mask shell 22. In the illustrated embodiment, rolling diaphragm 38 includes substantially circular, concentric outer rim 40 and inner rim 42 having a rolling element in the form of a flexible wall or membrane 44 therebetween. Rolling diaphragm 38 is preferably molded from a high modulus thermoplastic elastomer or rubbery material to provide the desired damping effect. The rolling diaphragm material may be the same or different material than the one used for seal member 20. In the illustrated embodiment, flexible membrane 44 has a generally uniform thickness and a substantially U-shaped cross-section when not under pressure, i.e., when the flow/pressure support system is not operating, or when not deflected, i.e., by relative movement between the seal member and the mask shell.

Rolling diaphragm 38 will change its shape depending on the force imparted to it through seal member 20 or mask shell 22. U-shaped flexible membrane 44, in this embodiment, is pointed away from mask shell 22 and in the direction of sealing member 20 when attached. Rolling diaphragm 38 isolates the forces acting on the mask shell and the seal member from one another and acts as a buffer between seal member 20 and mask shell 22. The rolling diaphragm also acts as a flexible joint allowing relative angular and displacement movement between seal member 20 and mask shell 22. Rolling diaphragm 38 isolates seal member 20 from movement of the patient's head and displacement of conduit tubing 14 or headgear.

Outer rim 40 of rolling diaphragm 38 includes an annular flange 46 extending substantially perpendicularly from a side wall 48 of the rolling diaphragm. Rolling diaphragm 38, in this illustrated embodiment, further includes four rectangular slots or holes 50 at the juncture of annular flange 46 and side wall 48. Inner rim 42 of the rolling diaphragm includes an integrally formed overmolding ring 52. Overmolding ring 52 includes a pair of oppositely positioned grooves including an inner groove 54 and an outer groove 56 forming an H-shaped cross section having a cross bar 58 with a plurality of rectangular through holes 60. During formation of the patient interface 10, rolling diaphragm 38 is molded first and then seal member 20 is over molded to inner groove 54 of overmolding ring 52. It is to be understood, however, that the present invention contemplates other configurations and techniques for coupling rolling diaphragm 38 to the seal member 20, such as gluing or mechanical fastening the components to one another.

Mask shell 22 is a generally rigid shell preferably formed from rigid plastic, such as polycarbonate. Mask shell 22 includes a patient side 62 and opposite thereto, an outer side 64. Mask shell further includes an annular portion 66 corresponding to the annular flange 46 of the outer rim 40 of the rolling diaphragm 38. Annular portion 66 of the mask shell in this embodiment includes four rectangular projections 68 for inserting into four rectangular holes 50 on outer rim 40 of the rolling diaphragm. Attached to outer side 64 of the mask shell is conduit coupling member 24 for coupling to delivery conduit 14. Conduit coupling member 24 allows 360 degree rotation to mask shell 22 and includes exhaust device 19.

In the illustrated exemplary embodiment, mask shell 22 has a generally circular bowl shape and includes headgear attaching elements 72 on outer side 64 thereof. Three socket attachment elements 72 are provided on this embodiment, each of which cooperates with a corresponding ball element (not illustrated) on headgear straps to attach the headgear strap to the mask shell. The ball and socket configuration, and other headgear attachment configurations suitable for use with the present invention, are disclosed in co-pending U.S. patent application Ser. No. 10/629,366 (Pub. No. 2004-0025883-A1), the contents of which are incorporated herein by reference. It is to be understood, however, that the present invention contemplates using any conventional connection assemblies to attach a headgear to the mask shell in this or any of the other embodiments.

The present invention contemplates the headgear that can be used with patient interface 10 can be any suitable headgear, i.e., any conventional headgear used in the patient interface field. For example, a typical headgear assembly comprises a headpiece (not shown) that overlies a portion of the patient's crania with headgear straps extending therefrom to adjustably connect the headgear to the mask.

In the illustrated embodiment, seal member 20 is a nasal cushion. It is to be understood, however, that the present invention contemplates nasal pillow, oral-nasal, or other known patient interfaces, as well, for use with the patient interface of this embodiment as well as the patient interfaces of the other embodiments.

Alternative exemplary embodiments of the patient interface of the present invention are illustrated in FIGS. 6-24. In these embodiments, many features are similar to those illustrated in FIGS. 1-5. Thus, the description of these embodiments will focus primarily on the features of the patient interface unique to each embodiment. These alternative embodiments are provided primarily to show the different configurations that are possible for the mask shell and rolling diaphragm. It is to be understood, however, that the present invention contemplates other configurations for the patient interface components as well as mixing and matching of the features of the patient interfaces illustrated in all of these embodiments.

Like the embodiment of FIGS. 1-5, a patient interface 78 according to a second embodiment of the present invention illustrated in FIGS. 6-9 includes a seal member 70, a mask shell 72, and a rolling diaphragm 80. In this embodiment, mask shell 72 and rolling diaphragm 80 are substantially triangular in shape. Rolling diaphragm 80 of this embodiment has an inner rim 82, which is circular or oval shaped. Of course, other shapes are contemplated by this invention. The rolling diaphragm is mounted to the mask shell with a retainer ring 74 that fits over an outer edge of the diaphragm and attaches to the mask shell.

Mask shell 72 includes a protruding portion 76 that extends from an upper portion of the mask shell, i.e., the portion of the mask shell that overlies the user's nose when the patient interface is donned on the user. In one embodiment of the present invention, protruding portion 76 includes a gas flow passage 77 that is adapted to be coupled to a patient circuit 14 for delivering the flow of gas to the interior of the patient interface. The present invention further contemplates providing a moveable conduit coupling member 81 that slideably attaches to protruding portion 76 so that the position of the conduit carrying the flow of gas can be adjusted relative to the mask shell, as indicated by arrow 79.

The present invention also contemplates that protruding portion 76 can function as a forehead support that extends from the upper portion of the mask shell for supporting the patient interface against the user's forehead. Although not shown in the figures, a forehead support member would attach to the protruding portion and support a cushion that contacts the user's forehead for supporting the patient interface on the user. The protruding portion can function as a forehead support alone or can be a combination a forehead support and coupling portion for the patient circuit.

Seal member 70 is attached to rolling diaphragm 80 by an overmolding ring 84. In this embodiment, overmolding ring 84 is a separate element from the rolling diaphragm 80. Overmolding ring 84 includes an inner ring 86 having a plurality of rectangular through holes 88, through which sealing member 70 is over molded. Overmolding ring 84 further includes an annular groove 87 to receive inner rim 82 of the rolling diaphragm.

Figure 1:
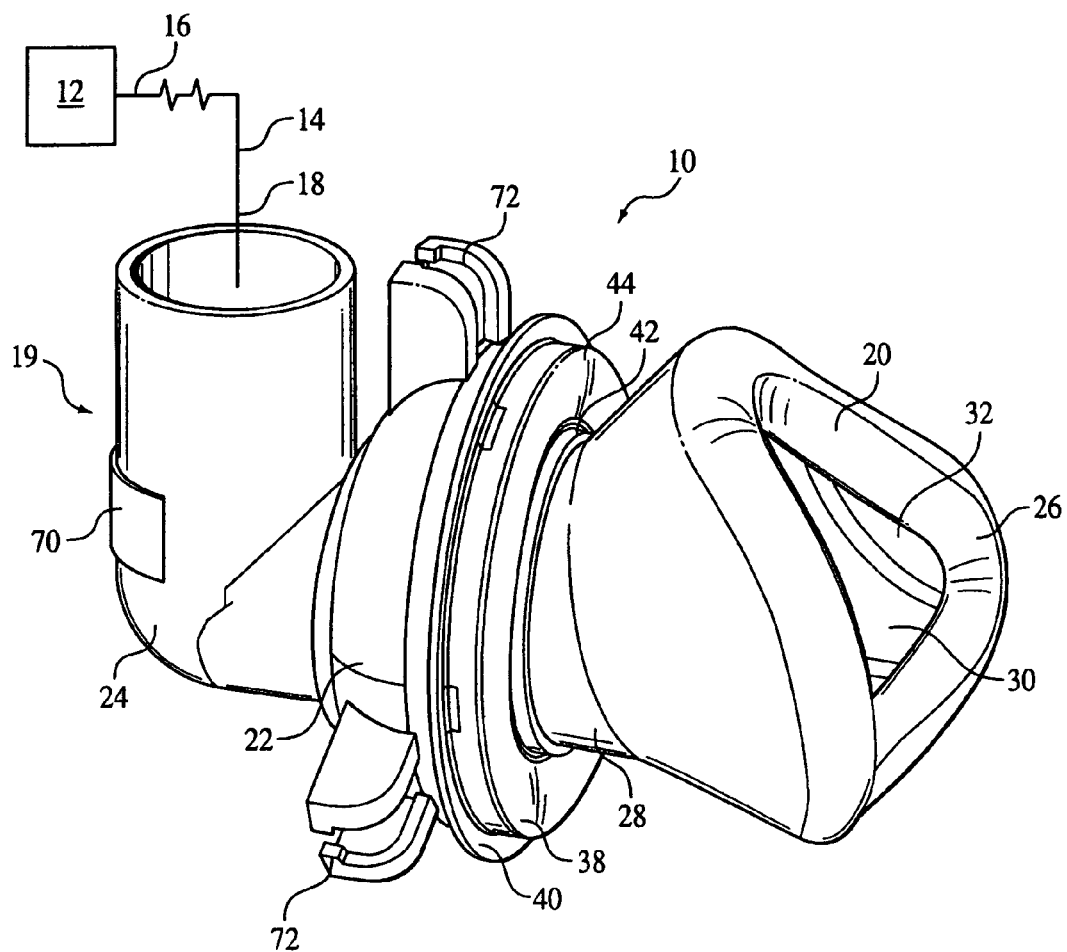
FIG. 1 is a perspective view of the patient interface according to the principles of the present invention shown schematically connected to a gas flow/pressure generating system.
Figure 2:
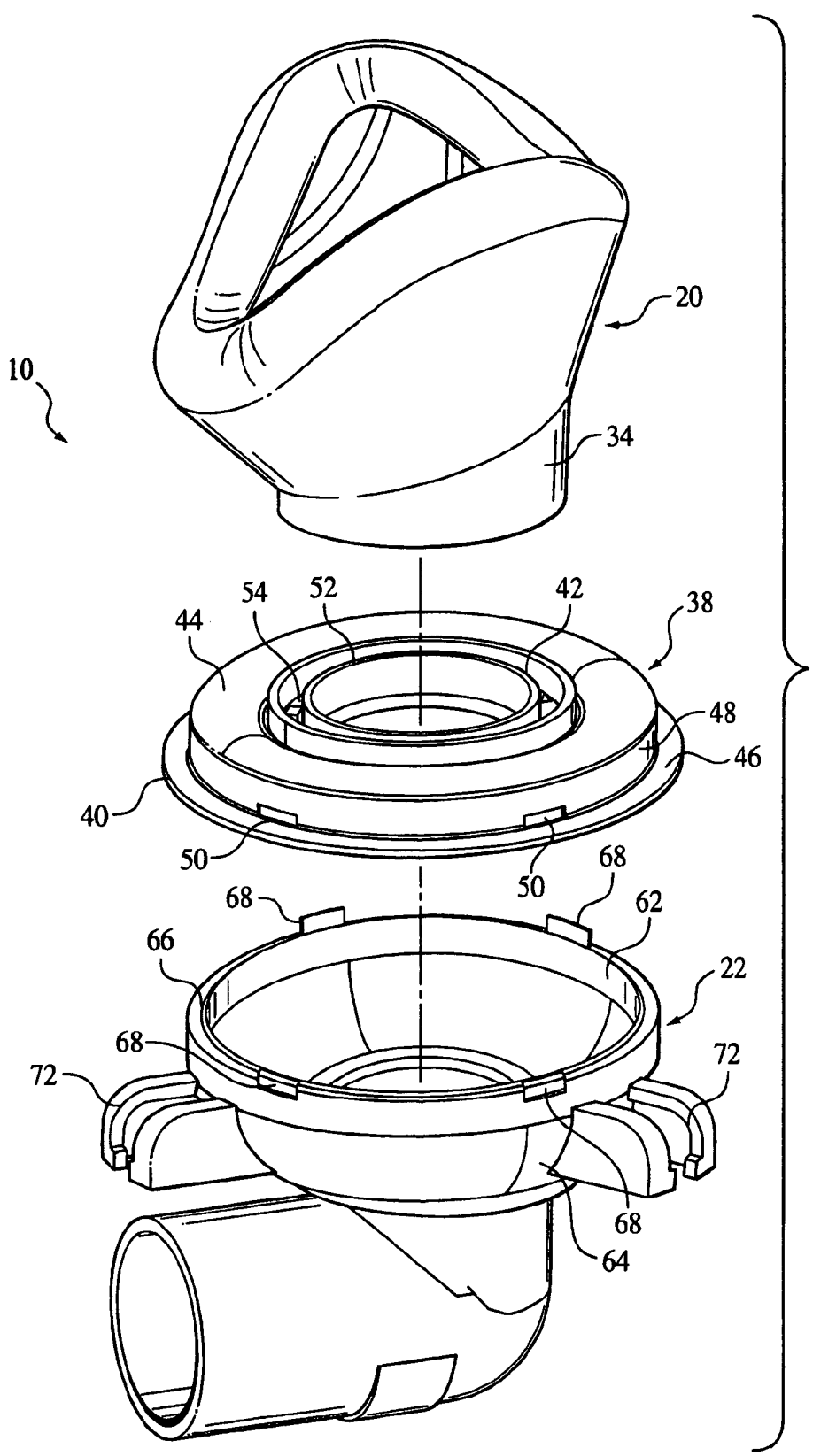
FIG. 2 is an exploded view of the patient interface of FIG. 1.
Figure 3:
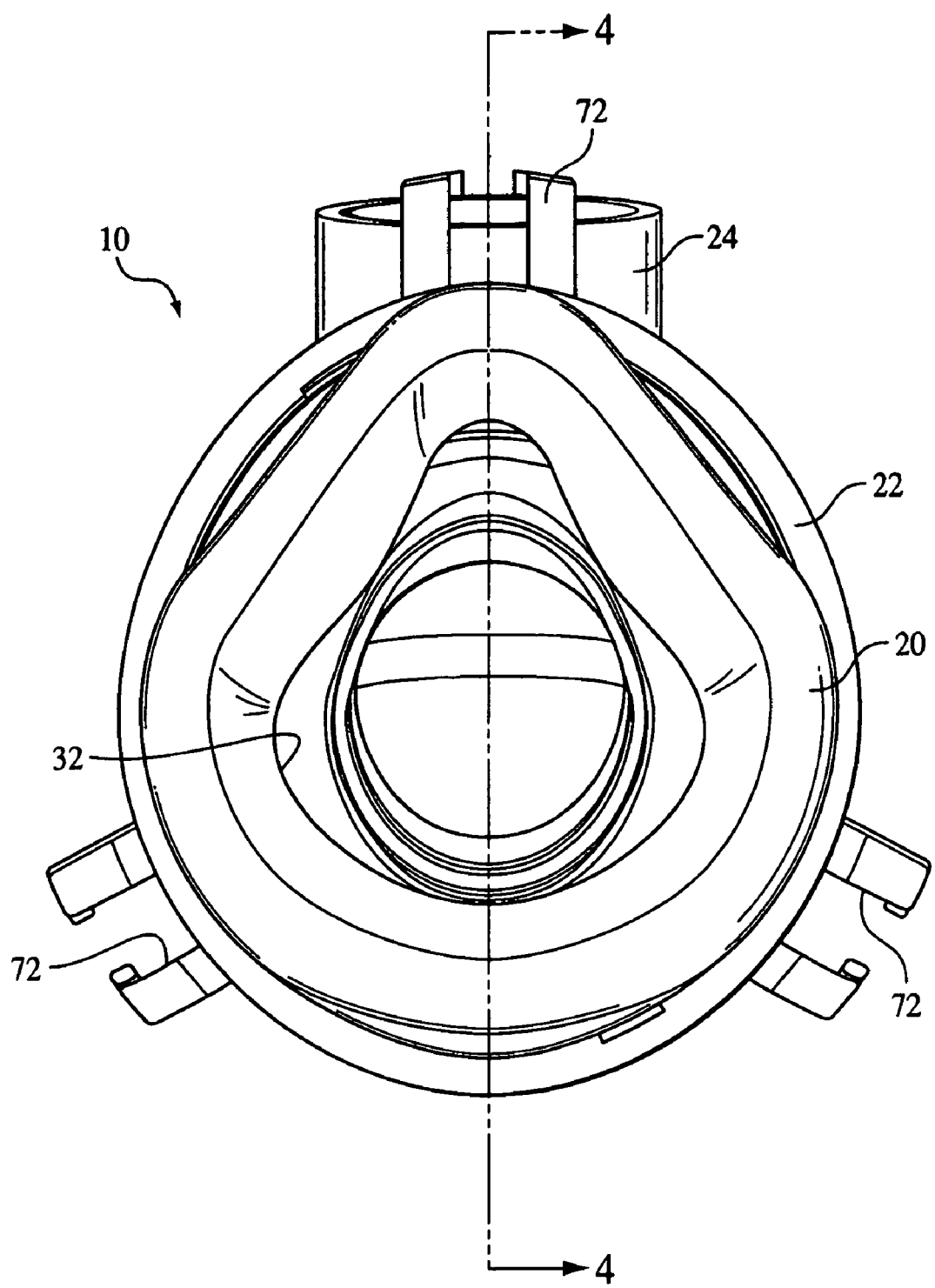
FIG. 3 is a front view of the patient interface of FIG. 1.
Figure 4:
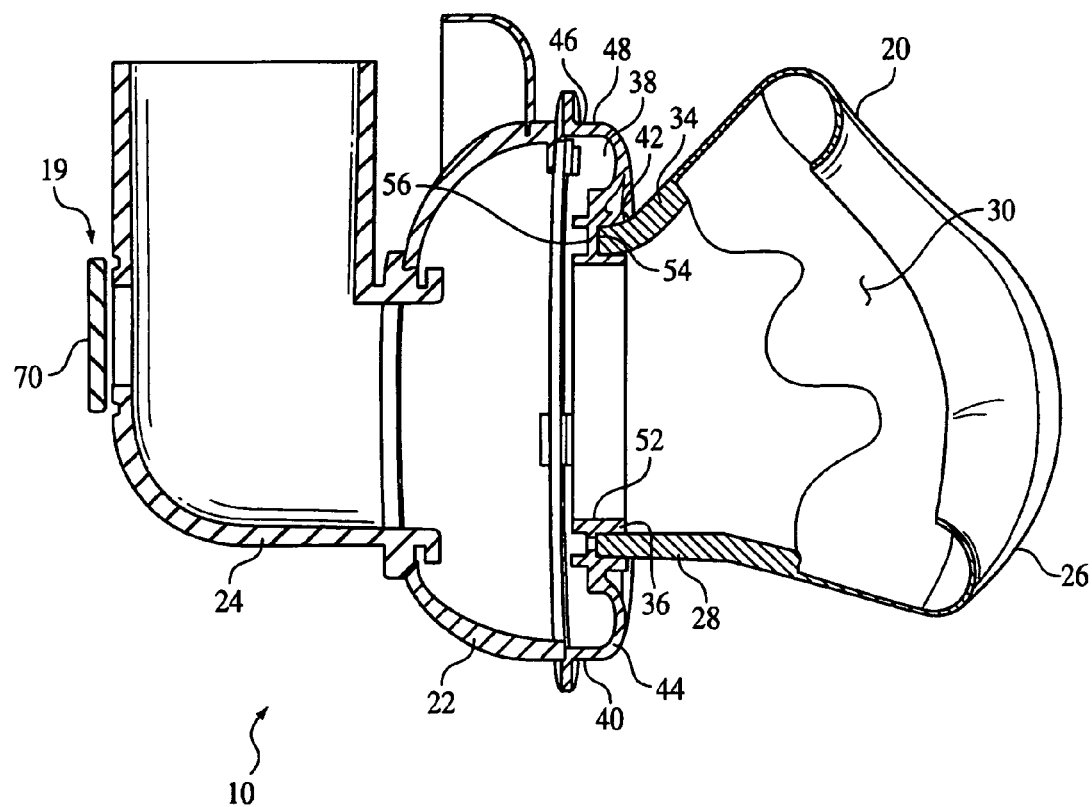
FIG. 4 is a sectional view of the patient interface of FIG. 1 taken along line 4-4 of FIG. 3.
Figure 5:
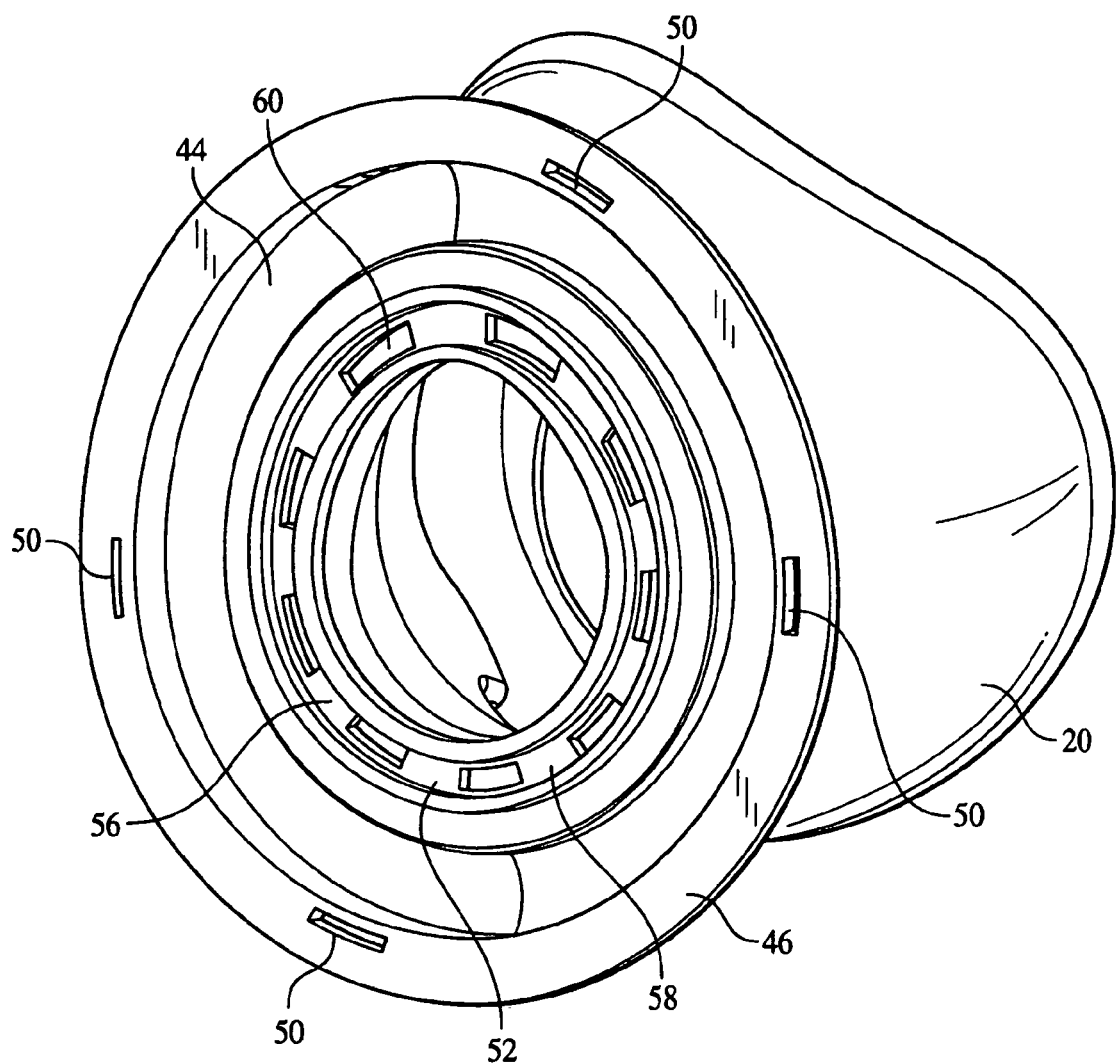
FIG. 5 is a rear perspective view of the seal member and rolling diaphragm of the patient interface of FIG. 1.
Figure 6:
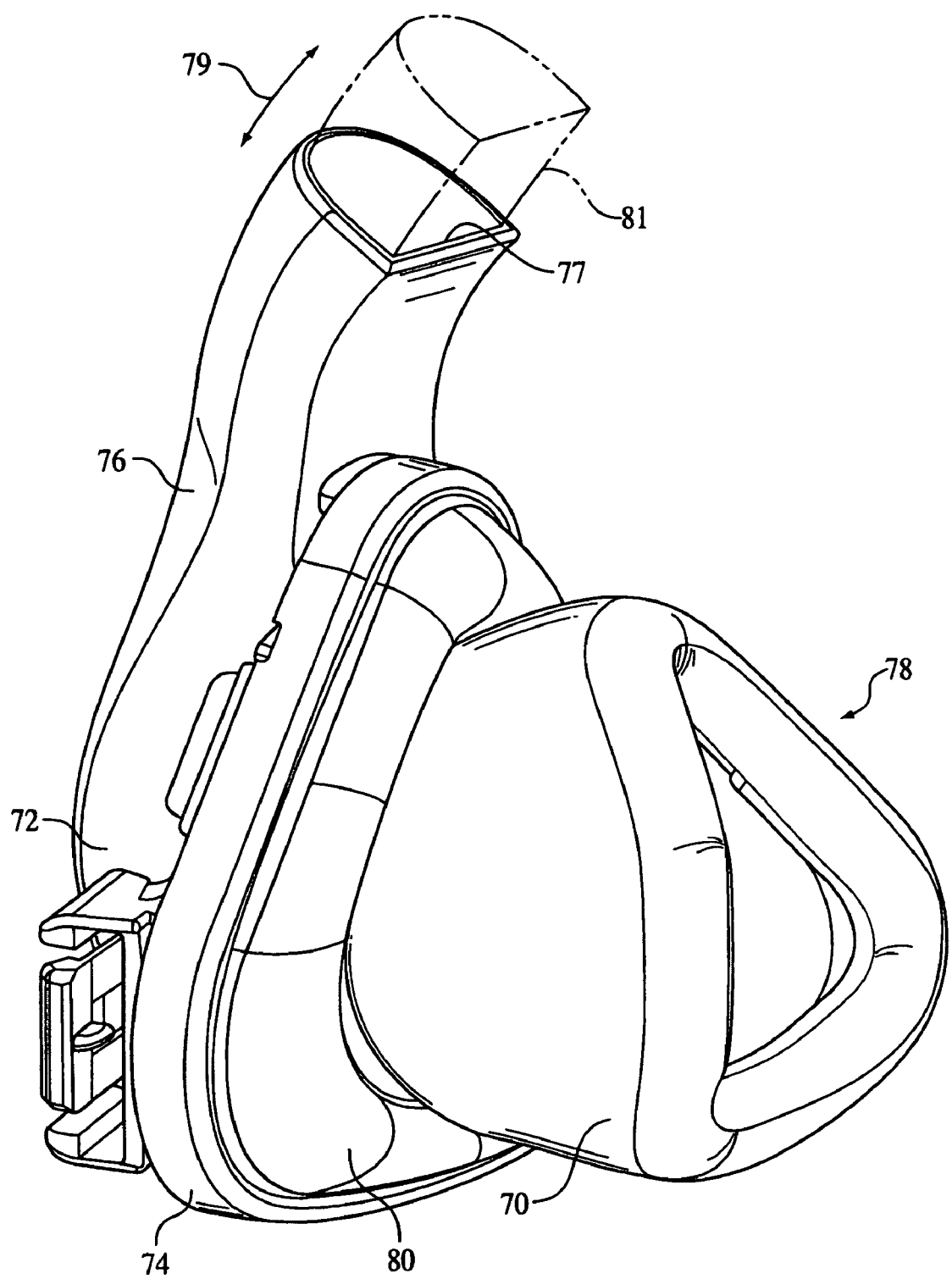
FIG. 6 is a perspective view of a second embodiment of a patient interface according to the principles of the present invention.
Figure 7:
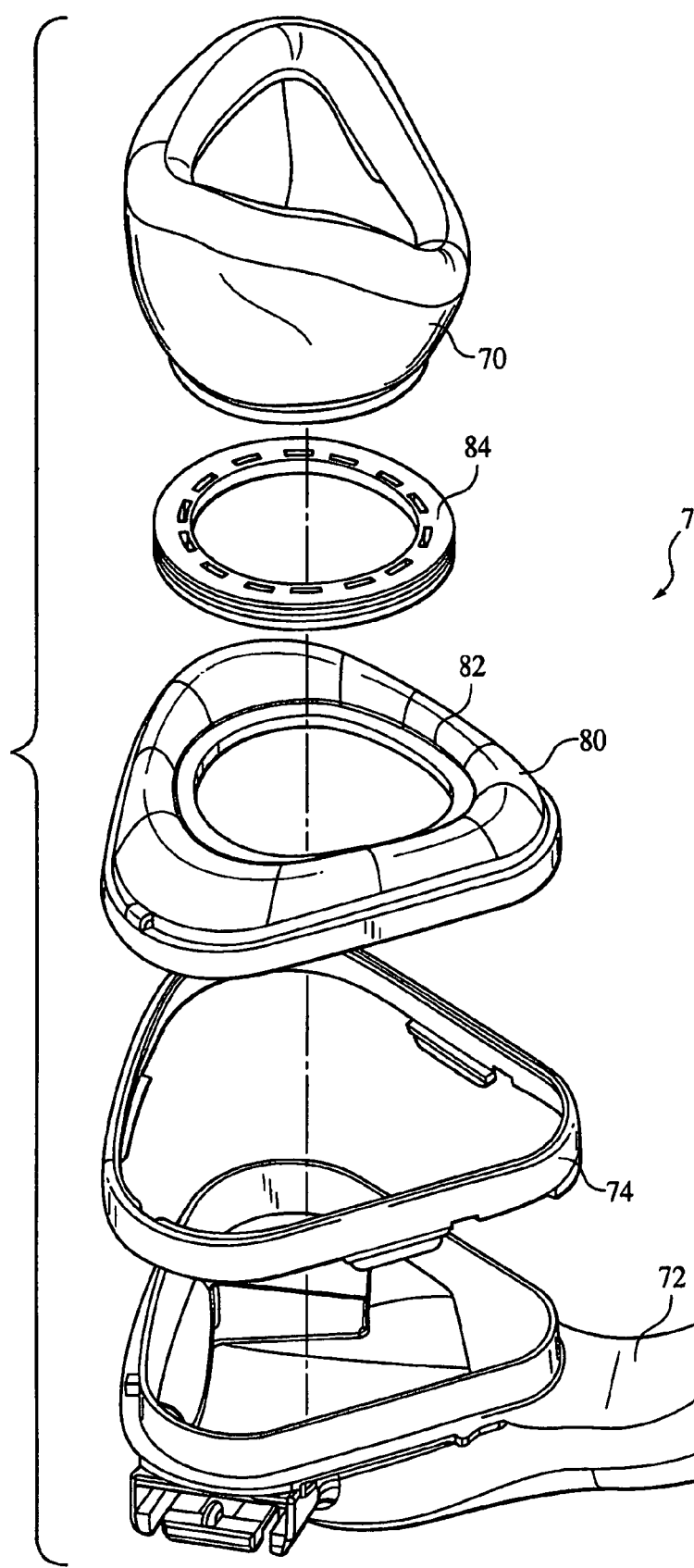
FIG. 7 is an exploded view of the patient interface of FIG. 6.
Figure 8:
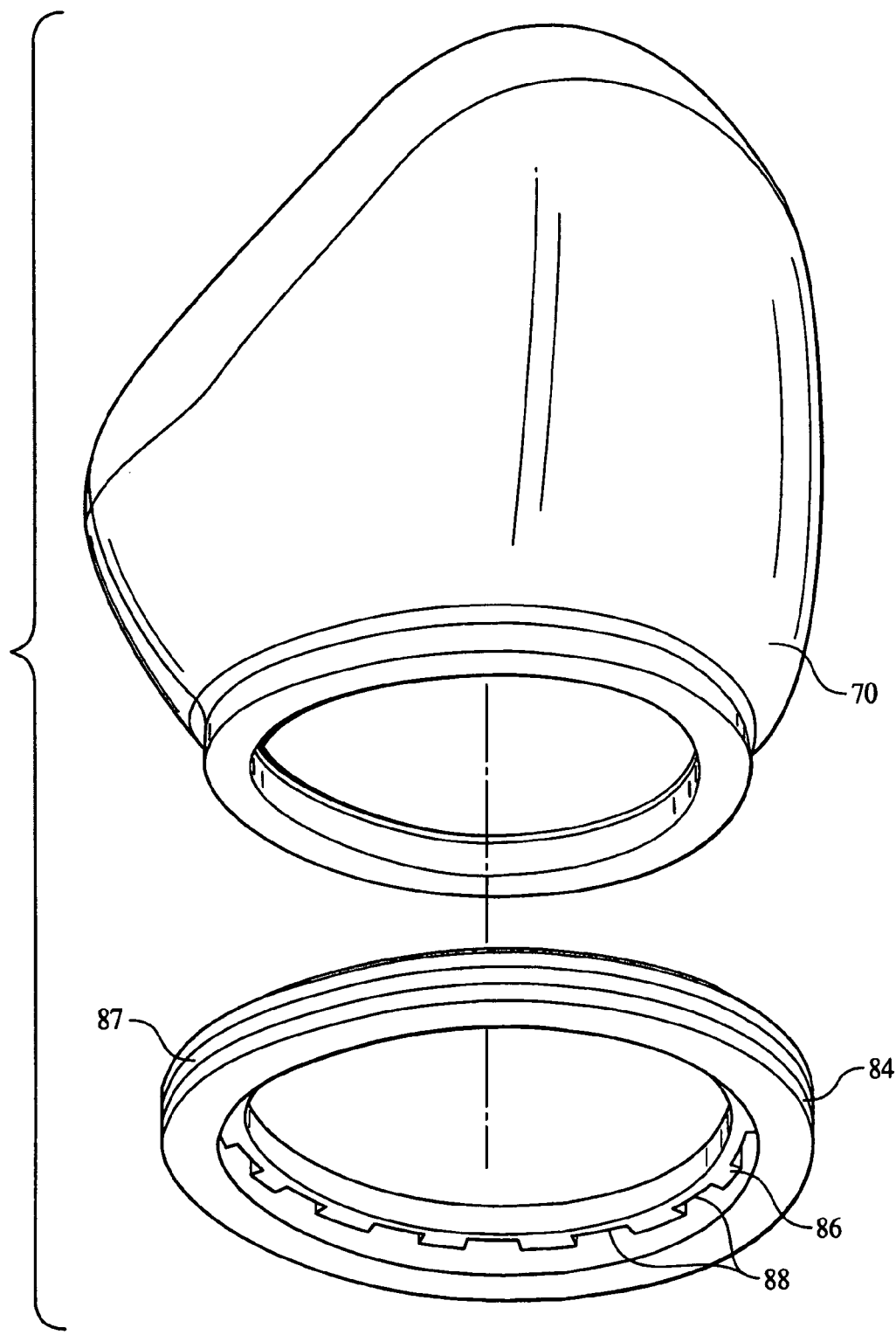
FIG. 8 is an exploded view of the seal member and overmolding ring of the patient interface of FIG. 6.
Figure 9:
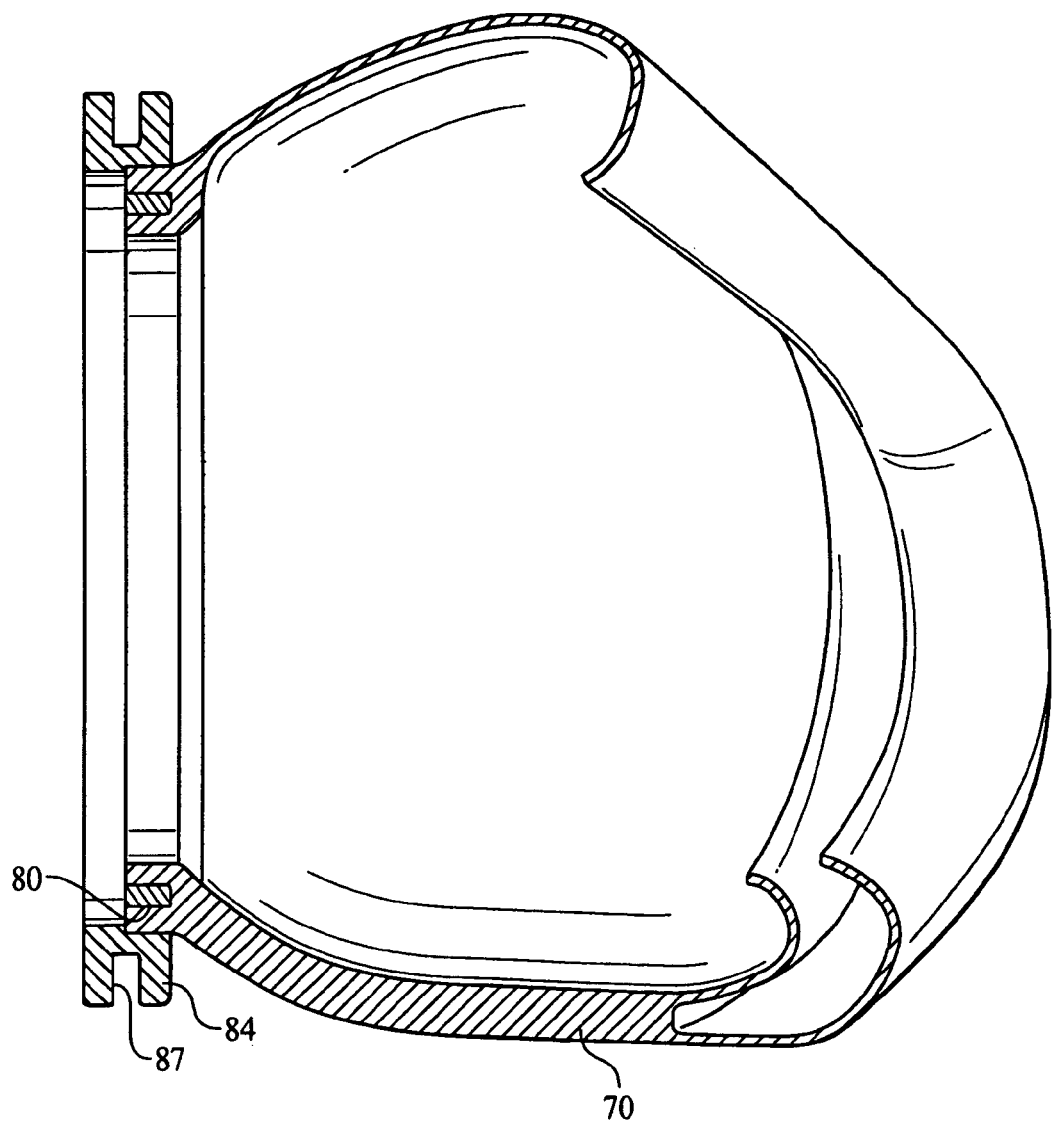
FIG. 9 is a side sectional view of the seal member and overmolding ring of the patient interface of FIG. 6.
Figure 10:
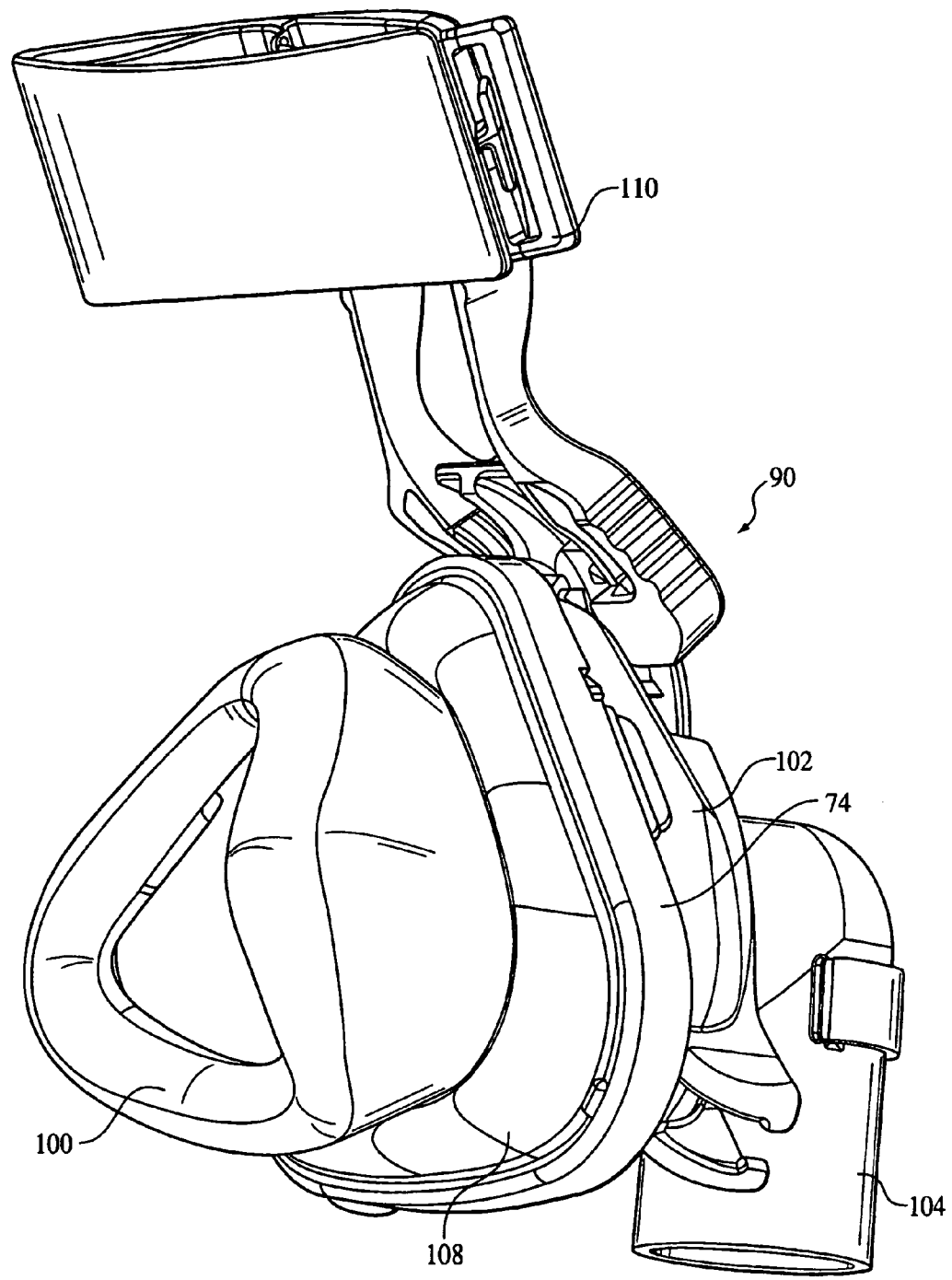
FIG. 10 is a perspective view of a third embodiment of the patient interface according to the principles of the present invention.
Figure 11:
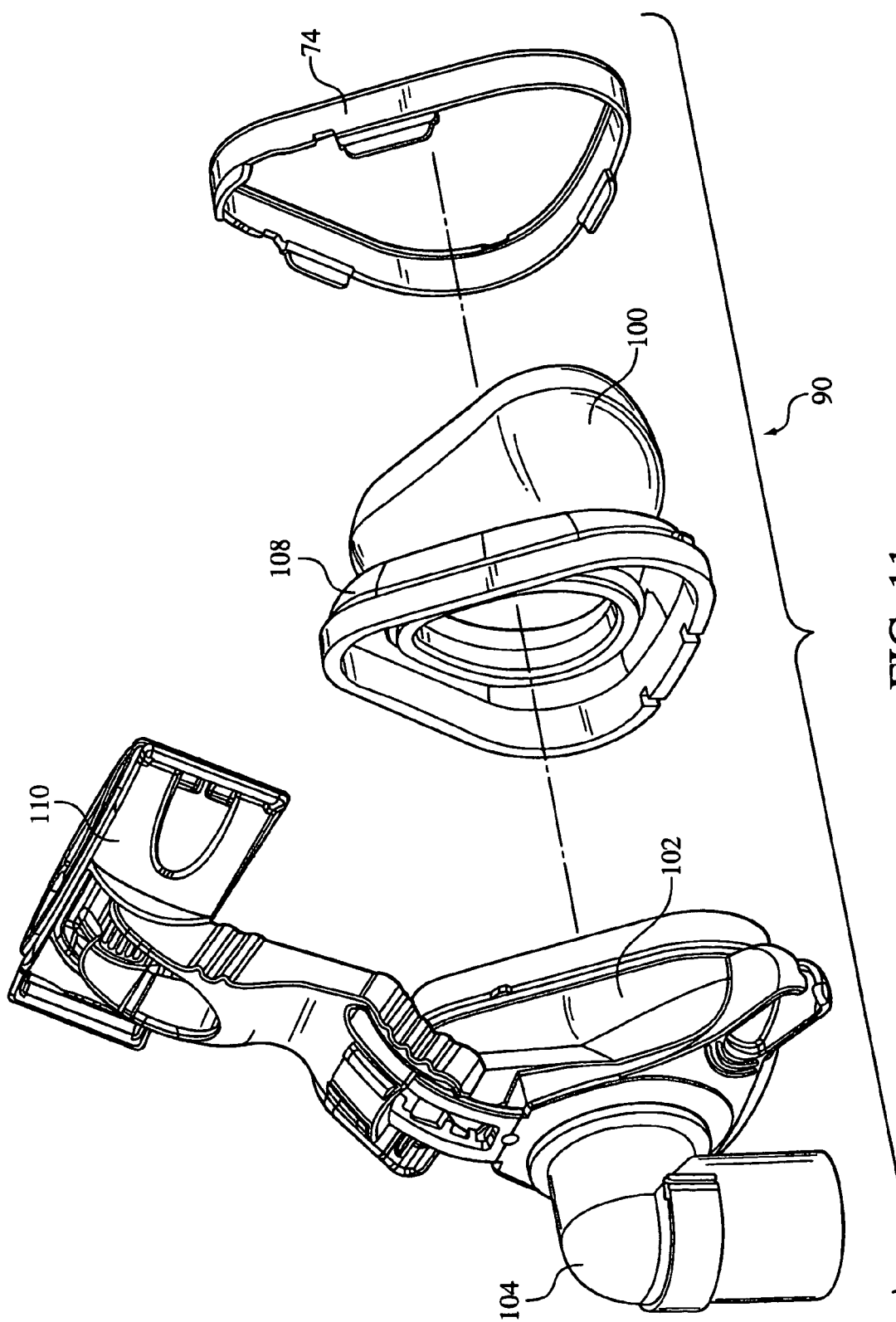
FIG. 11 is an exploded view of the patient interface of FIG. 10.
Figure 12:
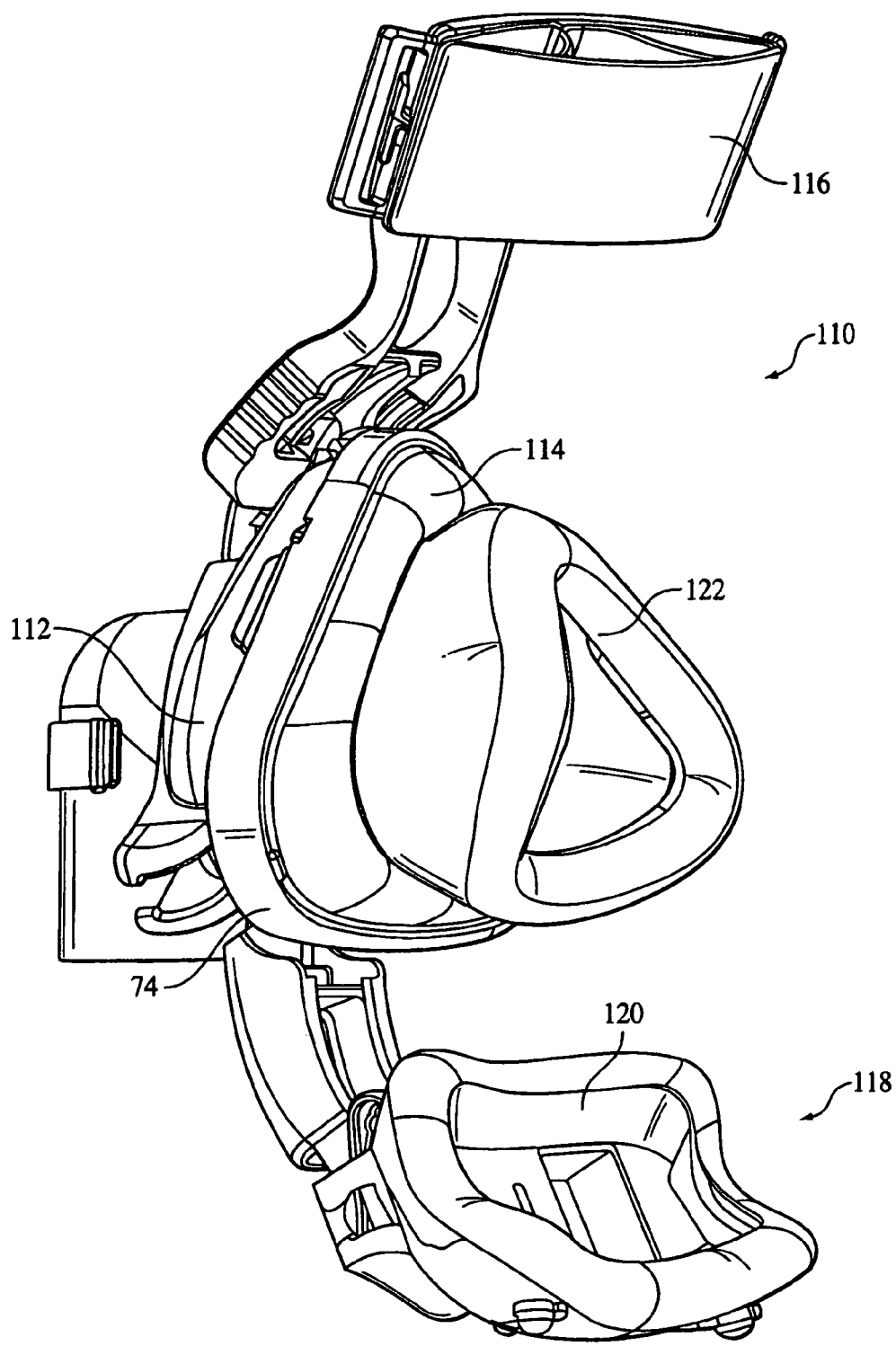
FIG. 12 is a perspective view according to a fourth embodiment of the patient interface according to the principles of the present invention.
Figure 13:
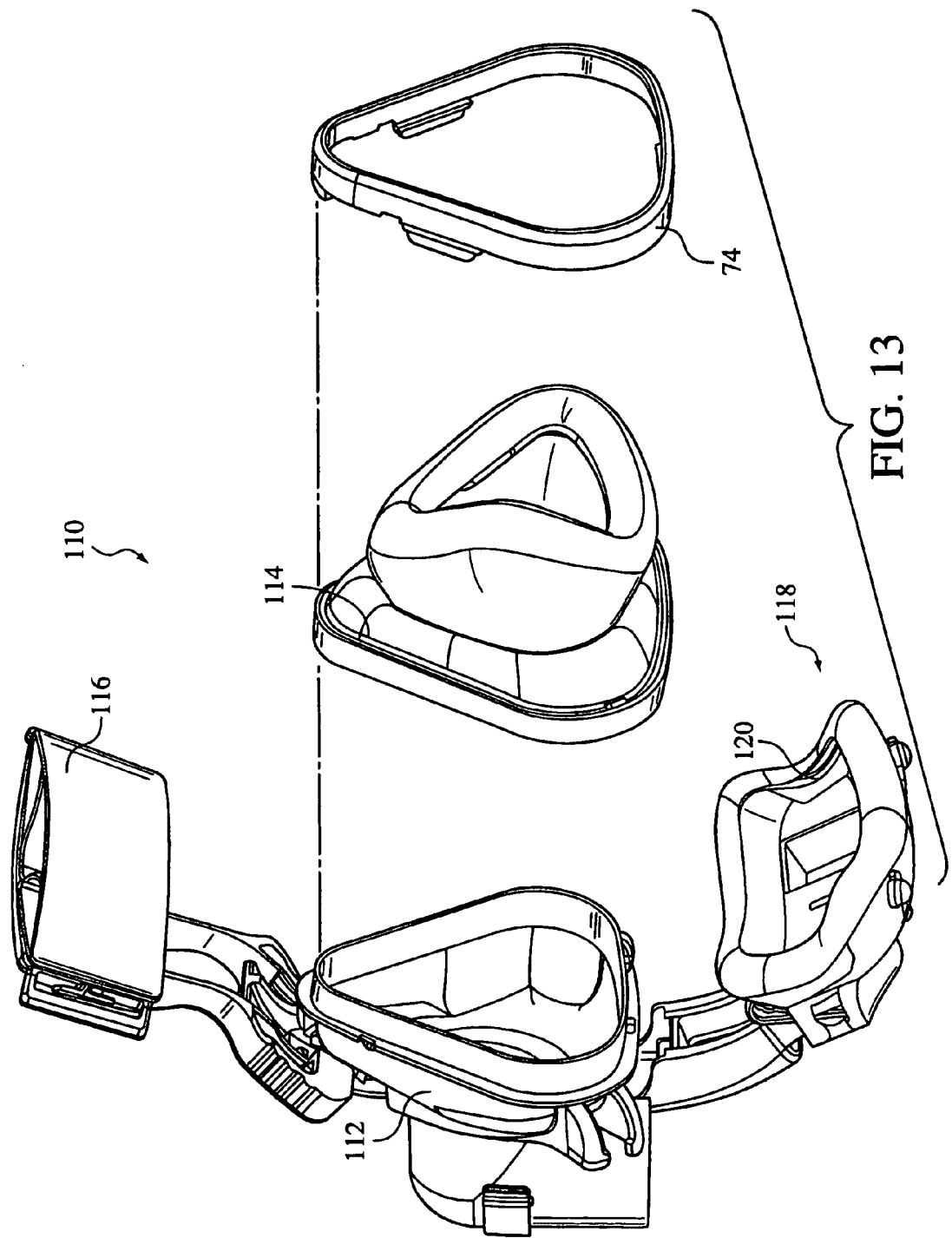
FIG. 13 is an exploded view of the patient interface of FIG. 12.
Figure 14:
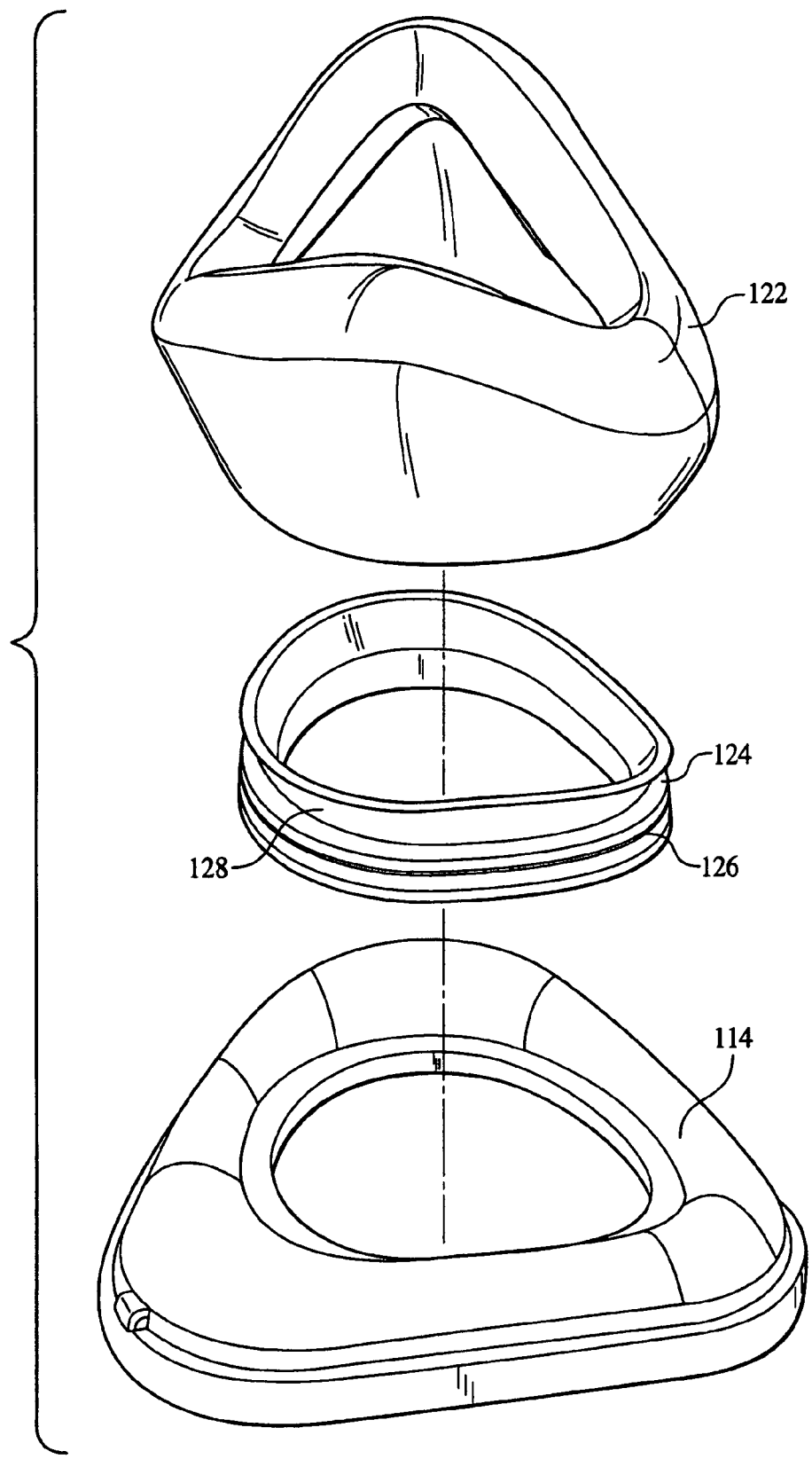
FIG. 14 is an exploded view of the sealing member, retainer ring, and rolling diaphragm of the patient interface of FIG. 12.
Figure 15:
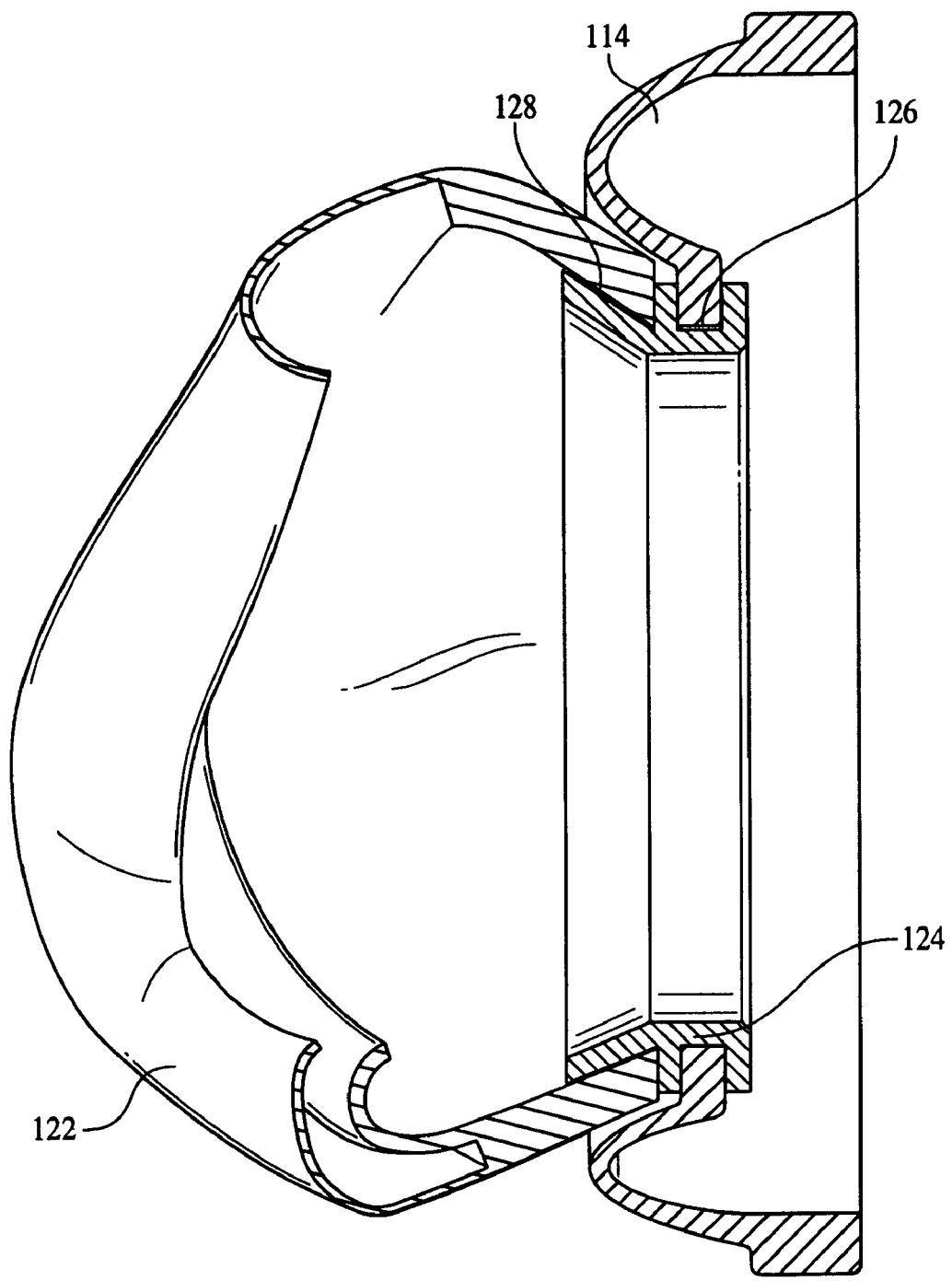
FIG. 15 is a side sectional view of the sealing member, retainer ring, and rolling diaphragm of the patient interface of FIG. 12.

Like the embodiment of FIGS. 1-5, a patient interface 90 according to a third embodiment illustrated in FIGS. 10-11 includes a seal member 100, a mask shell 102, a conduit coupling member 104, and a rolling diaphragm 108. Like the embodiment of FIGS. 6-9, mask shell 102 and rolling diaphragm 108 are substantially triangular in shape, and the rolling diaphragm and seal member assembly are attached to the mask shell via a retainer ring 74. Mask shell 102 of this embodiment, further includes an adjustable forehead support 110. A mask shell having such an adjustable forehead support is described in U.S. patent application Ser. No. 10/654,379 (Pub. No. US 2004-0045551-A1), the contents of which are incorporated herein by reference.

Like the embodiment of FIGS. 10-11, a fourth embodiment of a patient interface 110 illustrated in FIGS. 12-15 includes a mask shell 112 and a rolling diaphragm 114 that is substantially triangular in shape. The mask shell of this embodiment, however, not only includes an adjustable forehead support 116 but also an adjustable chin support 118. The mask shell corresponds to that described in U.S. patent application Ser. No. 10/953,642 (Pub. No. US 2005-0072428-A1), the contents of which are incorporated herein by reference. Mask shell 112 is essentially supported on the patient's face by forehead support 116 and chin support assembly 118. Forehead support 116 according to the illustrated exemplary embodiment is generally T-shaped. Chin support assembly 118, according to the illustrated exemplary embodiment, is also generally T-shaped. In the illustrated embodiment, chin support bracket is a cup-shaped member 120 that functions as the patient contacting cushion.

A seal member 122 is attached to diaphragm 114 by a sealing ring 124 having an outer annular groove 126 for receiving the inner rim of the rolling diaphragm 114 and an angled wall 128 for inserting into the interior of the neck portion of the seal member 122.

Figure 16:
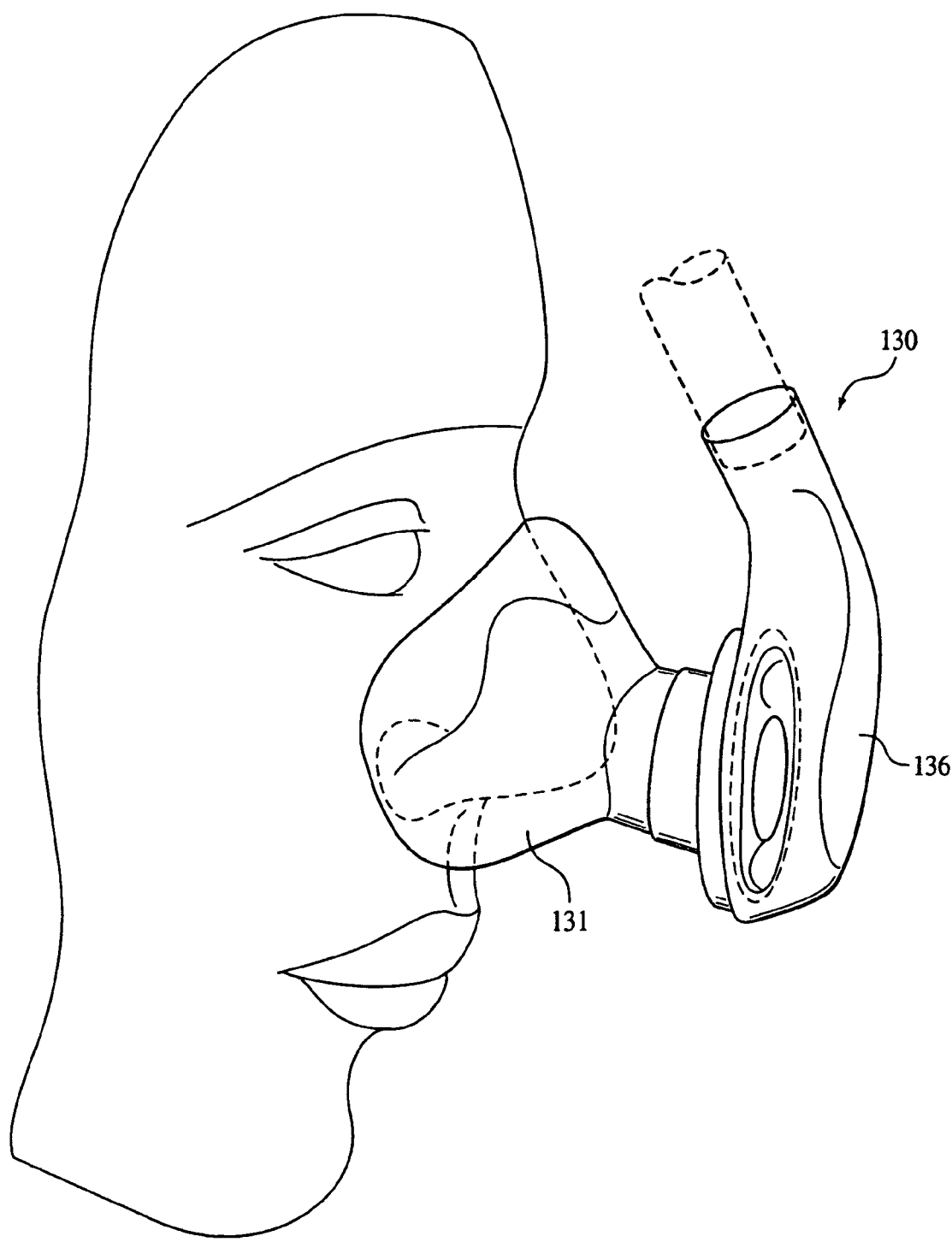
FIG. 16 is a perspective view according to a fifth embodiment of a patient interface according to the principles of the present invention shown worn on a patient.
Figure 17:
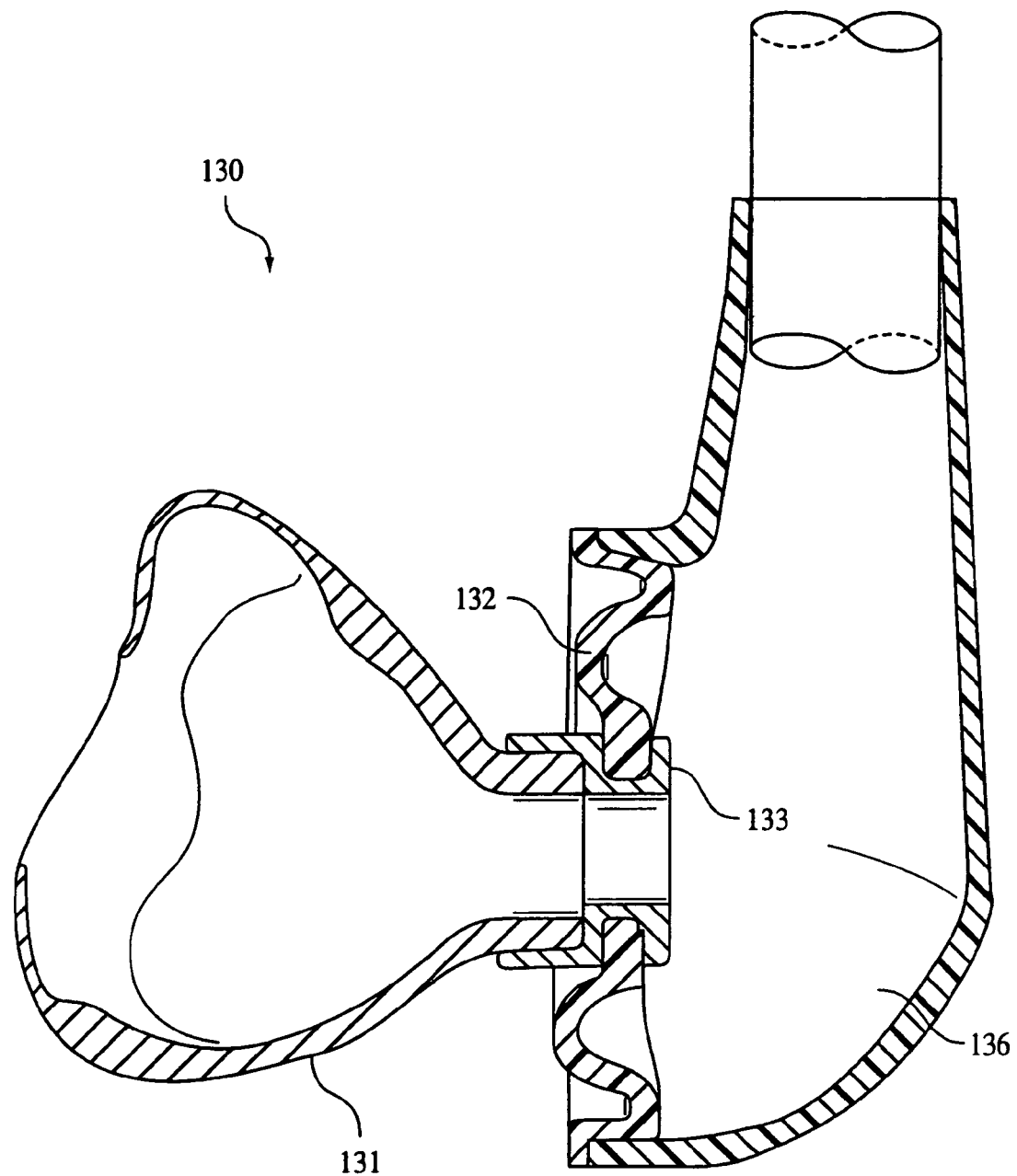
FIG. 17 is a side sectional view of the patient interface of FIG. 16.

Illustrated in FIGS. 16-17 is another embodiment of the patient interface 130 according to the principles of the present invention. Like the embodiment of FIGS. 1-5, a rolling diaphragm 132 in this embodiment is substantially circular. Patient interface 130 includes a mask shell that includes an integral spoon-like conduit coupling member 136. A seal member 131 is coupled to rolling diaphragm 132 via a connector 133. The present invention contemplates that connector 133 can also function as a swivel to allow rotational movement between conduit coupling member 136 and seal member 131.

FIG. 18 shows yet another embodiment of a patient interface 140 according to the principles of the present invention. Patient interface 140 includes a circular shaped rolling diaphragm (not shown) that couples a seal member 141 to a mounting member 142. Patient interface 140 is coupled to the patient with a headgear assembly 144. The details of the headgear assembly are disclosed in U.S. patent application Ser. No. 10/918,832 (Pub. No. US 2005-0076913-A1), the contents of which are incorporated herein by reference. Headgear assembly 144 includes an arm 146 that extends from a headgear strap 148 and connects to mounting member 142. A biasing mechanism 150 exerts a biasing force, as indicated by arrow 152, that urges the patient interface against the user's face. In this illustrated embodiment, mounting member 142 is coupled to arm 146 via a rotatable coupling 151, so that patient interface can rotate relative to the arm as indicated by arrow 153. This helps properly position the patient interface on the user.

Figure 19:
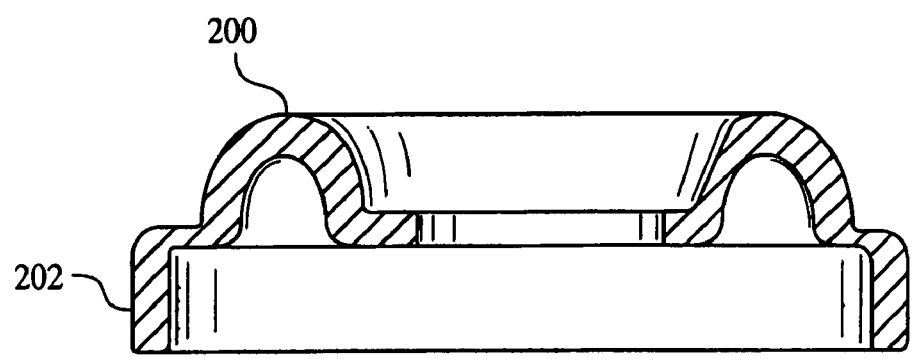
FIGS. 19-24 are sectional views of various embodiments of rolling diaphragms suitable for use in the patient interface of the present invention.
Figure 20:
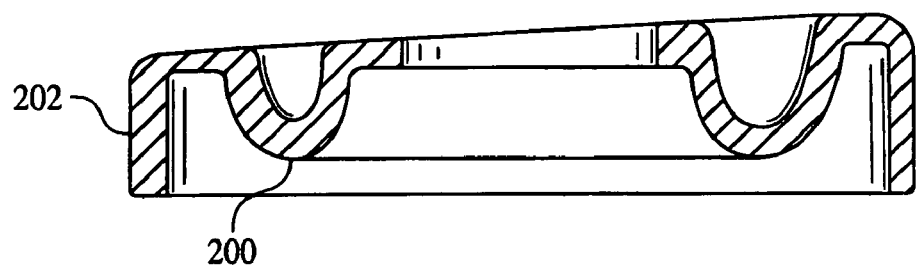
Figure 21:
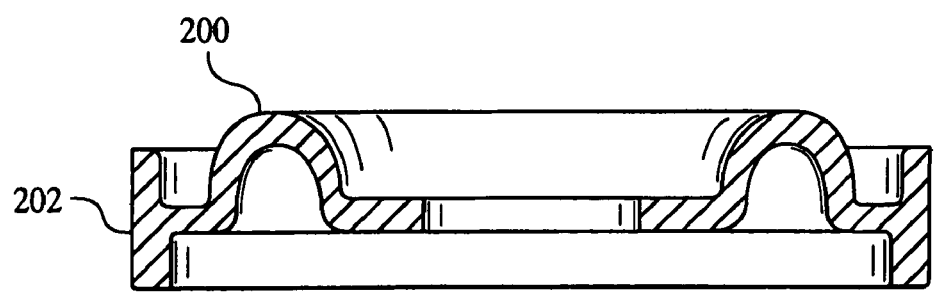

FIGS. 19-24 show variations of the rolling diaphragm contemplated by the present invention. More specifically, FIGS. 19-21 illustrate various orientations for a domed portion 200 in the rolling diaphragm. FIG. 19 shows dome 200 extending toward the seal member (not shown), which corresponds to the embodiment of the rolling diaphragm shown, for example, in FIG. 1. In this embodiment, the domed portion of the diaphragm is connected to the upper portion of a sidewall 202. FIG. 20 shows the domed area extending away from the seal member, i.e., toward the mask shell. FIG. 21 shows the domed area connected near the center or sidewall 202.

Figure 22:
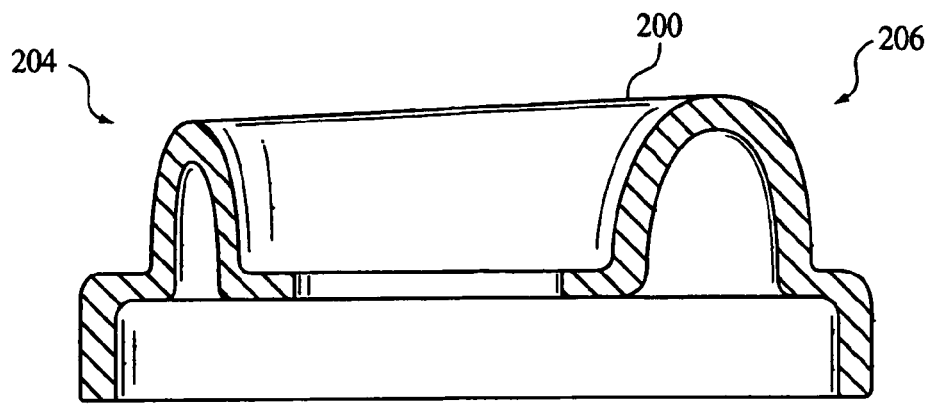

The present invention further contemplates that the domed area has either a varied height, wall thicknesses, curvatures, or any combination thereof to provide the desired flexible characteristics for the rolling diaphragm. That is, certain portions of the diaphragm can be configured to provide different degrees of flexibility. This is accomplished by configuring the rolling diaphragm such that a dimension of the rolling diaphragm at a first location around a perimeter of the rolling diaphragm is different from a corresponding dimension at a second location of the diaphragm to provide a different degree of flexibility for the diaphragm as between the first location and the second location. FIG. 22 illustrates a domed area 200 having a first curvature 204 and a second curvature 206 that is greater than the first curvature. The amount of curvature can control the amount of flexibility provided by the domed area. In general, the greater the curvature, the more flexible that portion of the rolling diaphragm.

Figure 23:
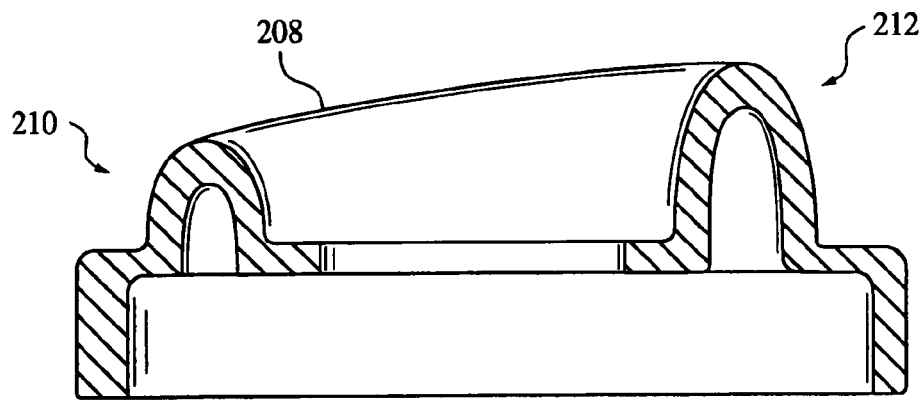

FIG. 23 illustrates a domed area 208 having a first height 210 and a second height 212 that is greater than the first height. The height of the dome area can control the amount of flexibility provided by the domed area. In general, the greater the height, the more flexible that portion of the rolling diaphragm.

Figure 24:
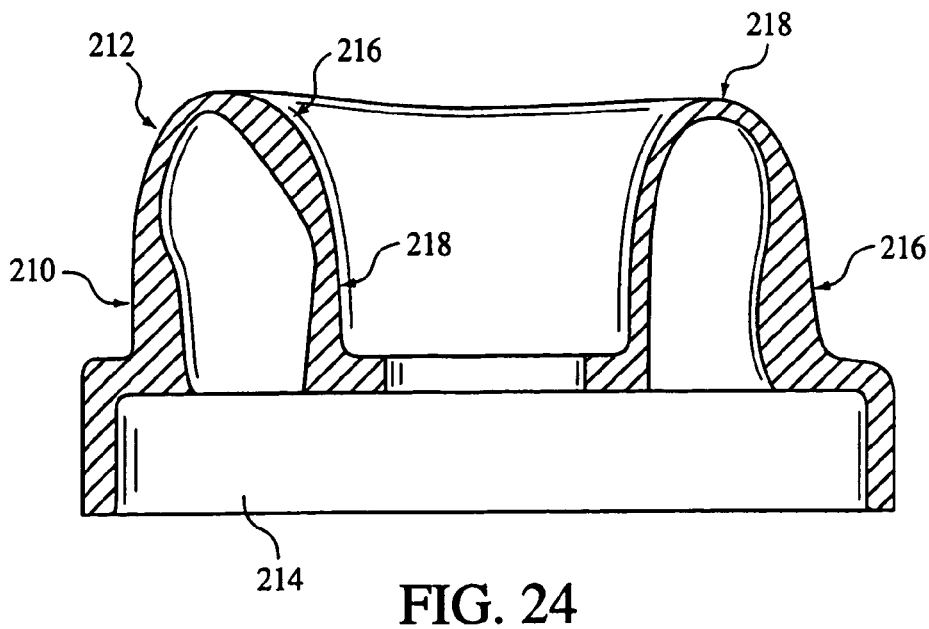

FIG. 24 illustrates a rolling diaphragm 214 having different wall thicknesses as different locations along the length of the rolling diaphragm. For example, diaphragm 214 includes thick regions 216 and thin regions 218.

Figure 25:
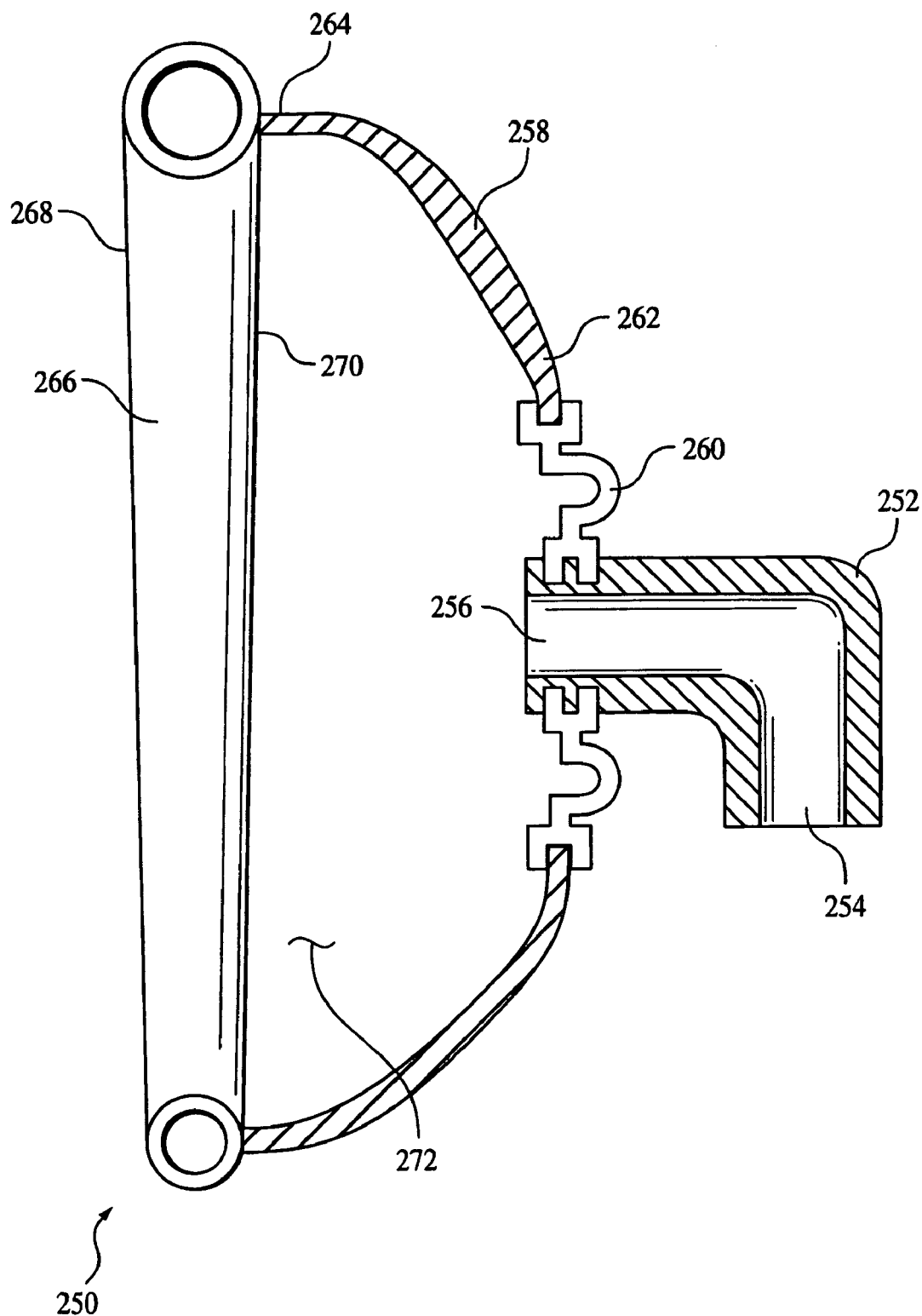
FIG. 25 is a side sectional view of a seventh embodiment of the patient interface according to the principles of the present invention.

FIG. 25 is a side sectional view of a seventh embodiment of the patient interface 250 according to the principles of the present invention. Patient interface 250 includes a conduit coupling member 252 having a first end portion 254 and a second end portion 256. A mask shell 258 is coupled to the conduit coupling member via a flexible connecting member 260. Mask shell 258 has a first side 262 and a second side 264 opposite the first side. A seal member 266 is coupled to second side 264 of the mask shell. Seal member 266 has a first end portion 268 that contacts a user's face when the patient interface is donned by the user and a second end portion 270 generally opposite the first end portion to which second side 264 of mask shell 258 is coupled. A cavity 272 is defined by the mask shell, the seal member, or both depending on the relative sizes of these components.

Flexible connecting member 260 is positioned between first side 262 of mask shell 258 and second end portion 256 of conduit coupling member 252 such that the flexible connecting member extends between the mask shell and the conduit coupling. As in the embodiments described above, the flexible connecting member allows angular movement between the mask shell and the conduit coupling member. The flexible connecting member can have any of the various configurations, materials, and properties described herein with respect to the other flexible connecting members. In addition, the present invention contemplates that the flexible connecting member can be rotateable relative to the conduit coupling member, the masks shell, or both.

Figure 26:
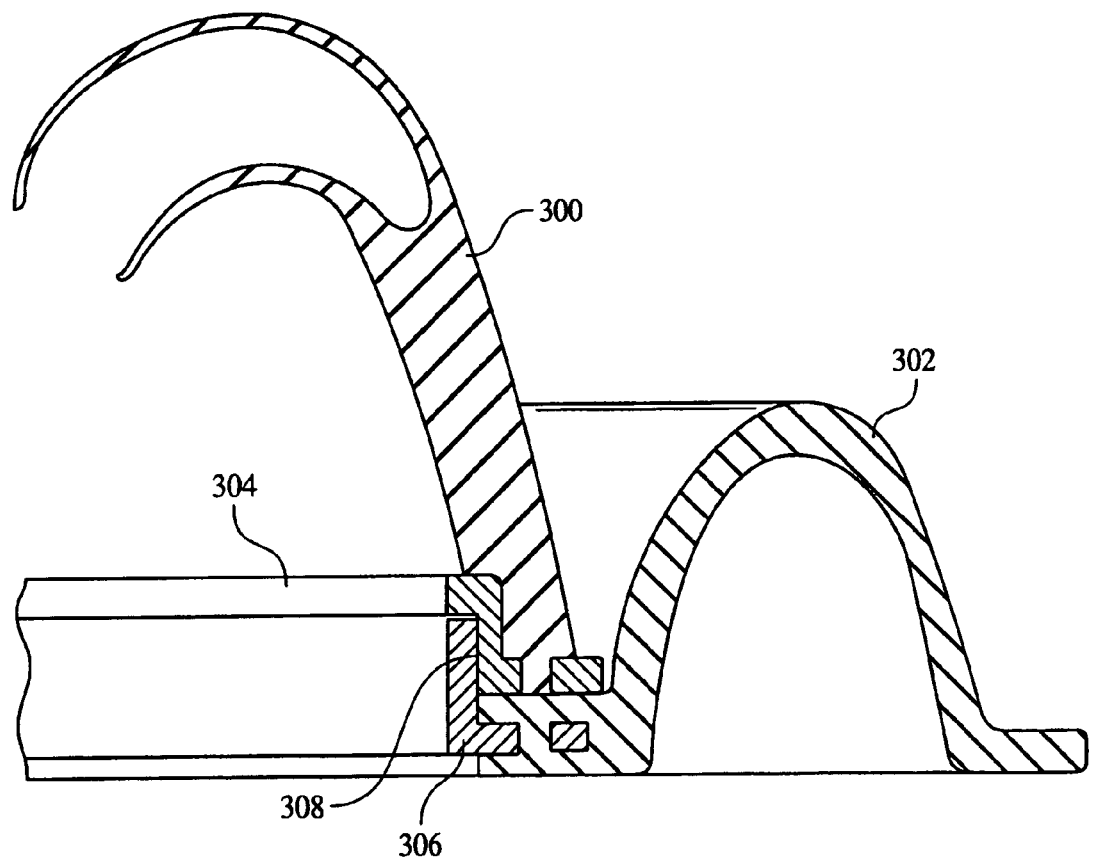
FIG. 26 is a detailed sectional view showing another technique for attaching a seal member to a flexible connecting member.

FIG. 26 is a detailed sectional view showing another technique for attaching a seal member 300 to a flexible connecting member 302. In this embodiment, the seal member is molded or otherwise bonded to a seal ring 304, and the flexible connecting member is molded or otherwise bonded to a connecting member ring 306. In an exemplary embodiment, the present invention contemplates overmolding seal 300 on ring 304 and overmolding flexible connecting member 302 on connecting member ring 306. Seal ring 304 and connecting member ring 306 are sized, configured and arranged such that a wall of the seal ring abuts or is close to a wall of the connecting member ring at a junction indicated by reference numeral 308. These walls are joined together using any conventional technique, such as sonic welding. Of course, friction alone can be used to maintain the rings in an assembled relation. It is to be understood that other configurations for the rings and ring/seal or ring/flexible member coupling are contemplated by the present invention.

The present invention also contemplates that different materials, or combinations of materials, can be used around the perimeter of the rolling diaphragm to control the degree of flexibility and the direction in which the diaphragm flexes. For example, a stiffened material can be provided at a location of the diaphragm where less flexibility is desired. The present invention further contemplates that structures, such as stiffening ribs, can be used to control the flexibility and direction of flex for the diaphragm.

It can also be appreciated that the description of the present invention, while discussing some different embodiments for the seal and mask, is not intended to be an exhaustive listing of the seals and masks suitable for use with the patient interface of the present invention. On the contrary, those skilled in the art can appreciate that the mask shell can have almost any configuration or size and still be used in conjunction with the patient interface of the present invention.

The patient interface of the present invention provides the patient with improved comfort. The present invention further provides a system for delivering a flow of gas to a patient that addresses the above identified concerns and that does not suffer from the shortcomings of conventional techniques. This is achieved by providing a system for delivering a flow of gas to a patient that includes a gas flow generating device capable of producing a flow of gas and a conduit having a first end portion operatively coupled to the gas flow generating device and a second end portion. The conduit carries the flow of gas from the gas flow generating device. The system includes a patient interface operatively coupled to the second end portion of the conduit and a headgear.

The rolling diaphragm allows for self-alignment of the cushion to the patient's face and passive adjustment of the patient interface. The rolling diaphragm acts as a buffer between the strapping support of the headgear and the cushion. The rolling diaphragm effectively isolates the sealing member of the patient interface from tubing and headgear movement. During sleep, a patient may alter his sleeping position which may cause his patient interface to dislodge from his face.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface comprising:
   a mask shell comprising a wall defining a cavity, wherein the wall has a first side, and wherein a first opening is defined generally in a first plane in the first side of the wall;
   a seal member having a first end portion adapted to contact a user's face and a second end portion opposite the first end portion, wherein the second end portion is disposed generally in the first plane;
   a flexible connecting member positioned between the first side of the wall and the second end portion of the seal member, wherein the flexible connecting member extends between the first side of the wall and the seal member generally in the first plane such that the flexible connecting member allows angular movement between the seal member and the mask shell and movement of the second end portion of the seal member into the cavity; and a substantially rigid ring positioned within the flexible connecting member and coupled between the flexible connecting member and the seal member, wherein the rigid ring, connecting member, and mask shell are configured such that at least a portion of the rigid ring is adapted to enter the first opening responsive to deflection of the connecting member.

2. The patient interface of claim 1, further comprising: a forehead support assembly associated with the mask shell, a chin support assembly associated with the mask shell, or both the forehead support assembly and the chin support assembly.

3. The patient interface of claim 1, wherein the flexible connecting member includes a generally U-shaped cross-section responsive to the flexible connecting member being in an undeflected position.

4. The patient interface of claim 3, wherein an apex of the U-shaped cross-section is directed in a first direction generally away from the mask shell or in a second direction generally toward the mask shell.

5. The patient interface of claim 1, wherein the flexible connecting member has a variable wall thickness.

6. A patient interface comprising:
a mask shell comprising a wall defining a cavity, wherein the wall has a first side, and wherein a first opening is defined in the first side of the wall;
a seal member having a first end portion adapted to contact a user's face, a second end portion opposite the first end portion, and a second opening defined in the second end portion, and wherein the first opening of the mask shell is larger than the second opening in the seal member;
a flexible connecting member positioned between the mask shell and the second end portion coupling the second end portion of the seal member with the first side of the mask shell, wherein the flexible connecting member enables movement of the second end portion of the seal member into the cavity; and
a substantially rigid ring positioned within the flexible connecting member and coupled between the flexible connecting member and the seal member, wherein the rigid ring, connecting member, and mask shell are configured such that at least a portion of the rigid ring is adapted to enter the first opening responsive to deflection of the connecting member.

7. The patient interface of claim 6, further comprising: a forehead support assembly associated with the mask shell, a chin support assembly associated with the mask shell, or both the forehead support assembly and the chin support assembly.

8. The patient interface of claim 6, wherein the flexible connecting member includes a generally U-shaped cross-section responsive to the flexible connecting member being in an undeflected position.

9. The patient interface of claim 8, wherein an apex of the U-shaped cross-section is directed in a first direction generally away from the mask shell or in a second direction generally toward the mask shell.

10. The patient interface of claim 6, wherein the flexible connecting member has a variable wall thickness.

11. A patient interface comprising:
a mask shell having a first side and a second side opposite the first side;
a seal member having a first end portion adapted to contact a user's face and a second end portion opposite the first end portion;
an annular flexible connecting member positioned between the mask shell and the second end portion of the seal member, wherein the connecting member connects the second end portion of the seal member with the first side of the mask shell, and wherein a dimension of the connecting member at a first location of a perimeter of the connecting member is different from a corresponding dimension at a second location of the perimeter to provide a different degree of flexibility for the connecting member between the first location and the second location; and
a substantially rigid ring positioned within the flexible connecting member and coupled between the flexible connecting member and the seal member, wherein the rigid ring, connecting member, and mask shell are configured such that at least a portion of the rigid ring is adapted to enter the first opening responsive to deflection of the connecting member.

12. The patient interface of claim 11, further comprising a forehead support assembly associated with the mask shell, a chin support assembly associated with the mask shell, or both the forehead support assembly and the chin support assembly.

13. The patient interface of claim 11, wherein the connecting member includes a generally U-shaped cross-section responsive to being in an undeflected position.

14. The patient interface of claim 13, wherein the dimension of the connecting member is (a) a distance from a base of the U-shape to an apex of the U-shape, (b) a distance from a first side of the U-shape to a second side of side of the U-shape, (c) a thickness of a wall of the U-shaped connecting member, or any combination of (a), (b), and (c).

15. The patient interface of claim 11, further comprising a substantially rigid ring coupled between the flexible connecting member and the seal member.

* * * * *